United States Patent
Fianchini et al.

(10) Patent No.: US 12,128,226 B2
(45) Date of Patent: Oct. 29, 2024

(54) DEVICE PARTICULARLY FOR MEDICAL USE AND STERILIZATION AND FILLING METHODS OF SUCH A DEVICE

(71) Applicant: AEA s.r.l., Angeli di Rosora-Ancona (IT)

(72) Inventors: Massimo Fianchini, Castelbellino (IT); Graziano Mattioli, Senigallia (IT)

(73) Assignee: AEA s.r.l., Angeli di Rosora-Ancona (IT)

( * ) Notice: Subject to any disclaimer, the term of this patent is extended or adjusted under 35 U.S.C. 154(b) by 641 days.

(21) Appl. No.: 16/845,389

(22) Filed: Apr. 10, 2020

(65) Prior Publication Data

US 2020/0324060 A1    Oct. 15, 2020

(30) Foreign Application Priority Data

Apr. 12, 2019    (IT) .................. 102019000005708

(51) Int. Cl.
| | |
|---|---|
| *A61M 5/50* | (2006.01) |
| *A61J 1/10* | (2006.01) |
| *A61J 1/20* | (2006.01) |
| *A61L 2/20* | (2006.01) |
| *A61M 5/315* | (2006.01) |
| *A61M 5/32* | (2006.01) |
| *A61M 5/31* | (2006.01) |

(52) U.S. Cl.
CPC .............. *A61M 5/5086* (2013.01); *A61J 1/10* (2013.01); *A61J 1/20* (2013.01); *A61L 2/20* (2013.01);
(Continued)

(58) Field of Classification Search
CPC ....... A61L 2202/24; A61M 2005/3106; A61M 39/20; A61M 5/3202; A61M 5/5086
See application file for complete search history.

(56) References Cited

U.S. PATENT DOCUMENTS

| | | |
|---|---|---|
| 2013/0164189 A1 | 6/2013 | Hadden |
| 2014/0052074 A1 | 2/2014 | Tekeste |
| (Continued) | | |

FOREIGN PATENT DOCUMENTS

| | | |
|---|---|---|
| CN | 101784450 A | 7/2010 |
| CN | 101939038 A | 1/2011 |
| (Continued) | | |

OTHER PUBLICATIONS

Italian Search Report dated Oct. 25, 2019.
(Continued)

*Primary Examiner* — William R Carpenter
(74) *Attorney, Agent, or Firm* — Blank Rome LLP

(57) ABSTRACT

The present invention relates to a device (100) comprising a body (1) defining a containment volume (2) for a fluid for medical use and equipped with a terminal (3) which defines a conduit (4) configured to put the containment volume (2) into communication with the outside. The device (100) comprises a cap support (10) integral with the body (1) and disposed outside the containment volume (2), the cap support (10) defining an internal volume (11) housing the terminal (3). The device (100) comprises a tip cap (20) associable with the cap support (10) by first constraint means (30) and associable with the terminal (3) by second constraint means (31). The tip cap (20) is configured to assume at least a first stable position and a second stable position.
In the first stable position, the tip cap (20) is integral with the cap support (10), in the first stable position a first portion (21) of the tip cap (20) being housed in the internal volume (11) of the cap support (10) and a second portion (22) of the tip cap (20) emerging from the internal volume (11) of the cap support (10). In the second stable position, the tip cap (20) is integral with the terminal (3) and is completely
(Continued)

housed in the internal volume (11) of the cap support (10). The containment volume (2) is in communication with the outside when the tip cap (20) assumes the first stable position and is sealed when the tip cap (20) assumes the second stable position.

26 Claims, 9 Drawing Sheets

(52) U.S. Cl.
CPC ...... *A61M 5/31513* (2013.01); *A61M 5/3202* (2013.01); *A61L 2202/182* (2013.01); *A61L 2202/24* (2013.01); *A61M 2005/3114* (2013.01); *A61M 2005/3125* (2013.01); *A61M 2205/0238* (2013.01)

(56) References Cited

U.S. PATENT DOCUMENTS

| | | | |
|---|---|---|---|
| 2016/0045629 | A1 | 2/2016 | Gardner et al. |
| 2016/0184529 | A1 | 6/2016 | Okihara |
| 2016/0262984 | A1 | 9/2016 | Arnott et al. |
| 2019/0091419 | A1 | 3/2019 | Hartung et al. |
| 2019/0217020 | A1* | 7/2019 | Okihara .............. A61M 5/3202 |

FOREIGN PATENT DOCUMENTS

| | | |
|---|---|---|
| CN | 109288568 A | 2/2019 |
| EP | 3042678 A1 | 7/2016 |
| EP | 3 388 098 A1 | 10/2018 |
| JP | H0928798 A | 2/1997 |
| JP | 2002172165 A | 6/2002 |
| JP | 2005-34419 A | 2/2005 |
| JP | 2010131064 A | 6/2010 |
| JP | 201378443 | 5/2013 |
| KR | 101692543 B1 | 1/2017 |
| WO | 2013047042 A1 | 4/2013 |
| WO | WO-2018061948 A1 * | 4/2018 .............. A61M 5/31 |

OTHER PUBLICATIONS

Office action issued Sep. 15, 2023 in Chinese Patent Application No. 202010287686.2 (with English translation).

Search Report issued Sep. 13, 2023 in Chinese Patent Application No. 202010287686.2 (with English translation).

* cited by examiner

DEVICE PARTICULARLY FOR MEDICAL USE AND STERILIZATION AND FILLING METHODS OF SUCH A DEVICE

RELATED APPLICATIONS

This application claims priority to Italian patent application number 102019000005708, filed on Apr. 12, 2019, the entirety of which is incorporated by reference herein in its entirety.

FIELD OF THE INVENTION

The present invention relates to a device suited for the storage and the selective delivery of fluid, in particular for medical use, for example a syringe. The device includes a closing system configured to allow or interrupt the communication between its internal volume and the outside.

PRIOR ART

Several technical solutions of disposable syringes suited for injecting medical fluids by means of a needle or a transfer duct are known in the medical field.

In particular, the U.S. Pat. No. 4,474,734 describes a pre-filled syringe in which a needle is fitted onto the output terminal. The needle is covered by means of a cap support fitted to the body of the syringe. The cap support is internally hollow and it is configured to work with a tip cap, consisting of a plug that can be inserted inside the cap support and a flange that always remains outside the cap support instead. The inner surface of the cap support and the outer surface of the tip cap are provided respectively with a series of ribs and a series of grooves geometrically compatible with each other. The tip cap can be positioned in a first stable position wherein the plug is only partially inserted in the cap support and in a second stable position wherein the plug is instead fully inserted in the cap support. The first stable position of the tip cap is adopted in order to subject the syringe needle to a sterilization treatment, while the second stable position of the tip cap is adopted in order to maintain the sterility of the syringe, there being an air-tight fit between the cap support and the tip cap. In fact, in the second stable position of the tip cap, the needle pierces the plug, so that the tip portion of the needle becomes imbedded in the end portion of the plug, thus creating the fit.

The technical solution disclosed in the U.S. Pat. No. 4,474,734 is advantageous, as it provides a syringe which can switch its configuration between a first unsealed configuration to perform a sterilization treatment of the syringe and a second sealed configuration for sealing the syringe and the medication within. However, this technical solution is deficient in that the tip cap presents considerable instability, above all in the second stable position, since in fact it is secured to the body of the syringe only by means of the needle perforation.

AIM OF THE INVENTION

A first objective of this invention is to solve the drawbacks of the U.S. Pat. No. 4,474,734, while maintaining the advantageous technical effects thereof.

A second objective of this invention is to significantly improve the stability of the tip cap, so that the air-tight fit of the containment volume of the syringe, once filled with the medication, is much more secure, reliable and robust.

A third objective of this invention is to prepare the syringe to be subjected to a sterilization treatment prior to filling, by providing a specific stable position of the tip cap (wherein the tip cap is integral with the cap support and does not prevent the containment volume of the syringe from communicating with the outside through the output terminal), and therefore being made hermetic by simply switching the position of the tip cap.

A fourth objective of this invention is to provide a supporting element for syringes which permits an optimal disposition of the syringes in a sterile container, thus providing proper transport and an optimal conservation of the aforementioned, and an optimal processing of the syringes for their filling, in particular by means of an automatic filling machine.

These objectives and others, which will appear better in the following description, are substantially achieved by a device, a sterilization method, a filling method and a supporting element in accordance with what expressed in one or more of the appended claims and/or following aspects, taken alone or in any combination with each other or in combination with any of the appended claims and/or in combination with any of the further aspects or characteristics described below.

SUMMARY

The preponderant aspects of the invention are set out below.

A 1st independent aspect of the present invention relates to a device (100) comprising:
- a body (1) defining a containment volume (2) for a fluid for medical use, said body (1) comprising a terminal (3), said terminal (3) defining a conduit (4) configured to put the containment volume (2) into communication with the outside;
- a cap support (10) integral with the body (1) and disposed outside the containment volume (2), said cap support (10) defining an internal volume (11) housing said terminal (3);
- a tip cap (20) associable with the cap support (10) by first constraint means (30) and associable with said terminal (3) by second constraint means (31), said tip cap (20) being configured to assume at least:
  - a first stable position in which the tip cap (20) is integral with the cap support (10), in said first stable position a first portion (21) of the tip cap (20) being housed in the internal volume (11) of the cap support (10) and a second portion (22) of the tip cap (20) emerging from the internal volume (11) of the cap support (10); and
  - a second stable position in which the tip cap (20) is integral with the terminal (3) and completely housed in the internal volume (11) of the cap support (10);
  - the containment volume (2) being in communication with the outside when the tip cap (20) assumes the first stable position and being sealed when the tip cap (20) assumes the second stable position.

A 2nd dependent aspect of the present invention relates to a device (100) wherein the first constraint means (30) define a releasable coupling between an inner lateral surface (12) of the cap support (10) and an external lateral surface (23) of the tip cap (20),
  said first constraint means (30) comprising at least one of the following:
  - at least one undercut defined between the tip cap (20) and the cap support (10); and an interference coupling, in particular a frictional coupling, between the tip cap (20) and the cap support (10).

A 3rd dependent aspect of the present invention relates to a device (100) wherein wherein the tip cap (20) and the cap support (10) have an axisymmetric structure, in particular a cylindrical structure, the first constraint means (30) comprising at least one circumferential groove (23a) formed on the outer lateral surface (23) of the tip cap (20), and one or more reliefs (12a) emerging from the inner lateral surface (12) of the cap support (10) towards the internal volume (11) of the cap support (10), said one or more reliefs (12a) being configured to engage, in particular to fit into, said at least one circumferential groove (23a) when the tip cap (20) is in the first stable position.

A 4th dependent aspect of the present invention relates to a device (100) wherein said one or more reliefs (12a) are arranged in the inner volume (11) of the cap support (10).

A 5th dependent aspect of the present invention relates to a device (100) wherein at least one of the external lateral surface (23) of the tip cap (20) and the inner lateral surface (12) of the cap support (10) has one or more recesses (40) defining, at least when the tip cap (20) is in the first stable position, one or more gaps between the tip cap (20) and the cap support (10).

A 6th dependent aspect of the present invention relates to a device (100) wherein said recesses (40) are formed on the inner lateral surface (12) of the cap support (10) and preferably angularly equally spaced apart, developing mainly along substantially parallel directions to an axis of symmetry of the cap support (10).

A 7th dependent aspect of the present invention relates to a device (100) wherein wherein the cap support (10) is integral with the body (11) of the device (100) by means of third constraint means (32) comprising at least one of the following elements:

at least one undercut defined between the cap support (10) and the body (1);

an interference coupling, in particular a frictional coupling, between the cap support (10) and the body (1);

one or more seals (50) placed between the cap support (10) and the body (1), so that the body (1) and the cap support (10) are joined seamlessly;

a coupling by gluing or welding between the cap support (10) and the body (1) of the device (100);

at least one label (60) made of sheet material, optionally made of paper or plastic sheet material, and/or a sheath, optionally made of preferably heat-shrinkable plastic material, placed between the cap support (10) and the body (1) of the device (100).

A 8th dependent aspect of the present invention relates to a device (100) wherein the body (1) comprises a collar (5) emerging from an extremal portion of the body (1) itself, said collar (5) being joined in one piece to the body (1) and at least partially surrounding the terminal (3), wherein optionally the collar (5) can have a cylindrical shape and be concentric with the terminal (3), said third constraint means (32) comprising at least one of an interference coupling, in particular a frictional coupling, or a gluing coupling between the inner lateral surface (12) of the cap support (10) and an outer lateral surface (5a) of the collar (5).

A 9th dependent aspect of the present invention relates to a device (100) wherein the tip cap (20) comprises an internal blind cavity (24) configured to receive by insertion, at least when the tip cap (20) is in the second stable position, at least one end portion of the terminal (3) to define a fluid-tight closing between the external environment and the containment volume (2), said blind cavity (24) being arranged in the first portion (21) of the tip cap (20) and oriented towards the terminal (3), at least one end portion (25) of the first portion (21) of the tip cap (20) being constrained by pressure, at least when the tip cap (20) is in the second stable position, between an external lateral surface (3c) of the terminal (3) and:

the inner surface (12) of the cap support (10); or an inner surface of a collar (5) emerging from the body (1) of the device, optionally the end portion (25) of the first portion (21) of the tip cap (20) comprising one or more raised ribs (29) configured to be connected to the inner surface (12) of the cap support (10) or to the inner surface of the collar (5) when the tip cap (20) is in the second stable position, said ribs (29) being configured to be deformed by squashing and developing along a longitudinal or transverse or helical path with respect to a symmetry axis of the tip cap (20).

A 10th dependent aspect of the present invention relates to a device (100) wherein the terminal (3) has a conical shape extending between a first end (3a) and a second end (3b), the terminal (3) being in particular a male Luer-type connector, wherein the first end (3a) is constrained to the body (1) of the device and has a first diameter, the second end (3b) being free and spaced from the first end (3a) and having a second diameter smaller than the first, A 11th dependent aspect of the present invention relates to a device (100) wherein the connector (3) has a conicity with an angle between 0.5 and 5° with respect to a central axis (A) of the connector (3), in particular an angle between 3.2 and 3.6°, again more in particular an angle equal to 3.44°.

A 12th dependent aspect of the present invention relates to a device (100) comprising one or more projections (12b) emerging from the inner surface of the cap support (10) and arranged in the internal volume (11) of the cap support (10), said projections (12b) being configured to:

allow the insertion of the tip cap (20) in the internal volume (11) of the cap support (10) and the transition of the tip cap (20) from the first to the second stable position; and prohibit or contrast the transition of the tip cap (20) from the second to the first stable position, A 13th dependent aspect of the present invention relates to a device (100) wherein, when the tip cap (20) is arranged in the second stable position, the end portion (26) of the second portion (22) abuts against a barrier plan (P) defined by the projections (12b), inhibiting or counteracting the transition of the tip cap (20) from the second to the first stable position, optionally the barrier plan (P) inhibiting or counteracting the axial movement of the tip cap (20) along the axis (A) of the terminal (3).

A 14th dependent aspect of the present invention relates to a device (100) wherein said projections (12b) and said reliefs (12a) emerge from the inner lateral surface (12) of the cap support (10) and are interposed between successive recesses (40) according to a preferably repeated angular pattern.

A 15th dependent aspect of the present invention relates to a device (100) wherein the tip cap (20) has a grip cavity (27) arranged at least partially at the second portion (22) of the tip cap itself, said gripping cavity (27) defining a concavity of the tip cap (20) delimited by perimetric walls (28) and configured to receive in thrust a coupling member for determining the transition of the tip cap (20) from the first to the second stable position.

A 16th dependent aspect of the present invention relates to a device (100) wherein the perimeter walls (28) of the tip cap (20) cooperate by friction, at least when the tip cap (20) is arranged in the second stable position, with the inner surface (12) of the cap support (10) to inhibit or counteract the transition of the tip cap from the second to the first stable position.

A 17th dependent aspect of the present invention relates to a device (100) wherein the tip cap (20) and the cap support (10) have a substantially cylindrical shape, the cap support (10) extending in thickness between an outer diameter and an inner diameter, wherein at least the second end portion (26) of the tip cap (20) has a larger diameter than the inner diameter of the cap support (10), so that the tip cap (20), when arranged in the second position, is joined by interference fit with the cap support (10), optionally the difference between the maximum diameter of the tip cap (20) and the inner diameter of the cap support (10) being between 0.01 mm and 2 mm, in particular, the maximum diameter being measured at the external lateral surface (23) of the second portion (22) of the tip cap (20), said diameters being measured when the tip cap and the cap support are separated from each other.

A 18th dependent aspect of the present invention relates to a device (100) wherein the tip cap (20) is made of a material whose elastic modulus is lower than the elastic modulus of the material constituting the cap support (10), in order to facilitate the interference fit of the tip cap (20) in the internal volume (11) of the cap support (10).

A 19th dependent aspect of the present invention relates to a device (100) wherein the tip cap (20) has:
  a structure made of a first material; and
  a coating made of a second material and arranged:
    on the side surface of the tip cap (23) to engage with the cap support (10) to define the first constraint means (30); and/or
    at the blind cavity (24) to define the second constraint means (31);
  the second material having a lower elastic modulus than the elastic modulus of the first material.

A 20th dependent aspect of the present invention relates to a device (100) wherein the tip cap (20) and the body (1), optionally the tip cap (20) and the cap support (10), are made of the same material, this material being a plastic material.

A 21st dependent aspect of the present invention relates to a device (100) wherein the third constraint means comprise a weakening portion interposed between the cap support (10) and the body (1) configured for, at least following an external tearing and/or twisting action exerted on the cap support (10), being damaged or broken to allow a condition of separation of the cap support (10) from the body (1) of the device and to highlight a tampering with the device (100), the third constraint means prohibiting a further engagement between the cap support (10) and the body (1) subsequently to the aforesaid tampering.

A 22nd dependent aspect of the present invention relates to a device (100) wherein said label (60) of sheet material and/or said sheath are placed to connect the cap support (10) with the body (1) of the device (100).

A 23rd dependent aspect of the present invention relates to a device (100) wherein the label (60) is glued at the turn of the body (1) and of the cap support (10) and/or wherein said sheath is shrunk at the turn of the body (1) and of the cap support (10).

A 24th dependent aspect of the present invention relates to a device (100) wherein said label (60) of sheet material and/or said sheath have at least one weakening portion, interposed between the cap support (10) and the body (1), configured so that, at least after an external tearing and/or twisting action exerted on the cap support (10), the label (60) will result damaged or broken, separating the cap support (10) from the body (1) and highlighting tampering with the device.

A 25th dependent aspect of the present invention relates to a device (100) wherein the seals (50) are placed to connect the cap support (10) with the body (1) of the device (100), defining at least a weakening portion, interposed between the cap support (10) and the body (1), configured so that, at least after an external tearing and/or twisting action exerted on the cap support (10), the seals (50) will result damaged or broken, separating the cap support (10) from the body (1) and highlighting tampering with the device.

A 26th dependent aspect of the present invention relates to a device (100) wherein the cap support (10) comprises, in correspondence with its own external side wall (13), a plurality of gripping projections (14) configured to allow or facilitate the grasping of the cap support (10) by a user and/or A 27th dependent aspect of the present invention relates to a device (100) wherein the cap support (10) comprises a plurality of beads (15) emerging from the inner side surface (12) of the cap support (10) and arranged in the inner volume (11) of the cap support itself, the beads (15) joining by interference an external lateral surface (5a) of the collar (5) defining at least part of the third constraint means (32).

A 28th dependent aspect of the present invention relates to a device (100) wherein the body (1), the terminal (3), the cap support (10) and the tip cap (20) have an axisymmetric shape with respect to a same axis (A), in particular being coaxial.

A 29th dependent aspect of the present invention relates to a device (100) wherein the collar (5) comprises a threaded coupling portion disposed on an inner lateral surface of the collar (5) itself, said threaded coupling portion being configured to:
  define an axial restraint with the first portion of the tip cap (20) when the latter is placed in the second stable position; and
  define an axial restraint with an auxiliary accessory, optionally a needle or a transfer duct, said auxiliary accessory being associable to the terminal (3) by a fluid-tight seal after removing the cap support (10) and the tip cap (20) from the device (100).

A 30th dependent aspect of the present invention relates to a device (100) wherein the body has a cylindrical shape extending for a length between 30 mm and 300 mm, and a diameter between 5 mm and 40 mm, said containment volume having in particular a maximum capacity between 1 ml and 200 ml, the body being made of a plastic material, preferably aseptic, pyrogen-free and transparent.

A 31st dependent aspect of the present invention relates to a device (100) wherein the tip cap (20) is at least partially, optionally entirely, made of elastomeric material, in particular rubber or silicone.

A 32nd dependent aspect of the present invention relates to a device (100) wherein the recesses (40) develop along a straight or helical path.

A 33rd dependent aspect of the present invention relates to a device (100) wherein the tip cap (20) comprises a centering protrusion (80) emerging from a bottom portion of the gripping cavity (27), and the centering protrusion (80) is entirely arranged in the gripping cavity (27) in correspondence of the axis of symmetry (A) of the tip cap.

A 34th dependent aspect of the present invention relates to a device (100) wherein an annular thrust surface is defined around said centering protrusion (80).

A 35th independent aspect of the present invention relates to a method of sterilization of a device (100), said device (100) comprising:
- a body (1) defining a containment volume (2) for a fluid for medical use, said body (1) comprising a terminal (3), said terminal (3) defining a conduit (4) configured to put the containment volume (2) into communication with the outside;
- a cap support (10) integral with the body (1) and disposed outside the containment volume (2), the cap support (10) defining an internal volume (11) housing the terminal (3);
- a tip cap (20) associable with the cap support (10) by means of first constraint means (30) and associable with the terminal (3) by means of second constraint means (31), this sterilization method comprising the following steps:
a) positioning the tip cap (20) in a first stable position in which the tip cap (20) is integral with the cap support (10), in said first stable position a first portion (21) of the tip cap (20) being housed in the internal volume (11) of the cap support (10) and a second portion (22) of the tip cap (20) emerging from the internal volume (11) of the cap support (10), so as to allow the containment volume (2) to communicate with the outside;
b) placing the device (100) inside a control volume;
c) infusing at least one sterilizing gas inside the control volume, so as to allow the passage of the sterilizing gas from the control volume to the containment volume (2) of the device (100).

A 36th dependent aspect of the present invention relates to a sterilization method of a device (100) wherein a further step occurs between phases a) and b), namely the aspiration of at least part of a gas, in particular air, present inside the control volume.

A 37th dependent aspect of the present invention relates to a sterilization method of a device (100) wherein the transit of the sterilizing gas in step c) takes place through one or more recesses (40) formed in at least one of the external lateral surface (23) of the tip cap (20) and the inner lateral surface (12) of the cap support (10).

A 38th independent aspect of the present invention relates to a method for filling a device (100), said device (100) comprising:
- a body (1) defining a containment volume (2) for a fluid for medical use, said body (1) comprising a terminal (3), said terminal (3) defining a conduit (4) configured to put the containment volume (2) into communication with the outside;
- a cap support (10) integral with the body (1) and disposed outside the containment volume (2), said cap support (10) defining an internal volume (11) housing the terminal (3);
- a tip cap (20) associable with the cap support (10) by means of first constraining means (30) and associable with the terminal (3) by means of second constraining means (31), this filling method comprising the following steps:
i) removing the tip cap (20) from the device (100), starting from a first stable position in which the tip cap (20) is integral with the cap support (10), in such first stable position a first portion (21) of the tip cap (20) being located in the internal volume (11) of the cap support (10) and a second portion (22) of the tip cap (20) emerging from the internal volume (11) of the cap support (10);
ii) connecting in a fluid-tight seal the terminal (3) of the device (100) with a filling terminal, said filling terminal being in particular in fluid communication with a bag carrying a fluid of interest;
iii) transferring a predetermined quantity of the fluid of interest in particular from the bag to the containment volume (2) of the device (100);
iv) disconnecting the filling terminal from the terminal (3) of the device (100);
v) arranging the tip cap (20) in a second stable position in which the tip cap (20) is integral with said terminal (3) and completely housed in the internal volume (11) of the cap support (10), so as to seal tightly the containment volume (2).

A 39th dependent aspect of the present invention relates to a method for filling a device (100), said device further comprising a plunger (70) fluid-tight inserted inside the body (1) to define a closing portion of the containment volume (2), the plunger (70) being movable along the axis (A) of the body (1) in order to vary the capacity of the containment volume (2), wherein step iii) is performed by activating said plunger (70).

A 40th dependent aspect of the present invention relates to a method for filling a device (100), wherein the second stable position of the tip cap (20) in step v) is a position such that a subsequent removal of the tip cap (20) can take place only by leaving evidence of tampering.

A 41st independent aspect of the present invention relates to a supporting element, in particular a plate (200), having at least one through opening (201) configured to receive a syringe in insertion, characterised by comprising positioning means (202) suitable to house the syringe in at least one through opening (201) exclusively according to two predetermined angular orientations substantially with a phase shift of 180°.

A 42nd dependent aspect of the present invention relates to a supporting element, wherein the positioning means (202) define cavities for housing lobed portions (90) of the syringe, in particular for a pair of gripping tabs associated with an extremal portion of the body (1) of the syringe.

A 43rd dependent aspect of the present invention relates to a supporting element, comprising a plurality of through openings (201) each configured to hold a syringe and arranged in a row along at least one predetermined trajectory, wherein at least part of the through openings (201) are delimited by at least one first and second positioning wall (204a, 204b) emerging from the support element and facing each other to define at least part of the positioning means (202), the combination of the first and second positioning wall defining a groove (205) extending between extremal portions of the support element along an undulating trajectory to define a plurality of housing cavities at least partly shaped complementarily to the lobed portions (90) of the syringes.

A 44th dependent aspect of the present invention relates to a supporting element defining a plurality of grooves (205) arranged side by side and divided by a wall between the first and the second positioning wall.

A 45th independent aspect of the present invention relates to a container (300) comprising a bottom (301) and side walls (302) raising from the bottom (301) to define an internal volume, the side walls (302) extending between an attachment portion with the bottom to a free end portion, said container (300) being configured to hold, at the free end portion of the side walls (302), at least one supporting element according to claim 16 or claim 17, in such a way that the supporting element extends along a surface at a distance from a plan of extension of the bottom (301) of the container (300), A 46th dependent aspect of the present invention relates to a container (300), including coupling means configured to allow the reception of the supporting element only at a predetermined position and/or at a predetermined orientation, A 47th dependent aspect of the present invention relates to a container (300), wherein the coupling units comprise at least one protrusion (305) configured to be located in a corresponding recess (206) obtained in the supporting element or at least a recess configured to receive a corresponding protrusion emerging from the supporting element.

BRIEF DESCRIPTION OF THE DRAWINGS

Some embodiments and some aspects of the invention will be described below with reference to the attached drawings, provided for indicative and therefore non-limiting purposes only wherein.

DETAILED DESCRIPTION

Device

Figure 9:
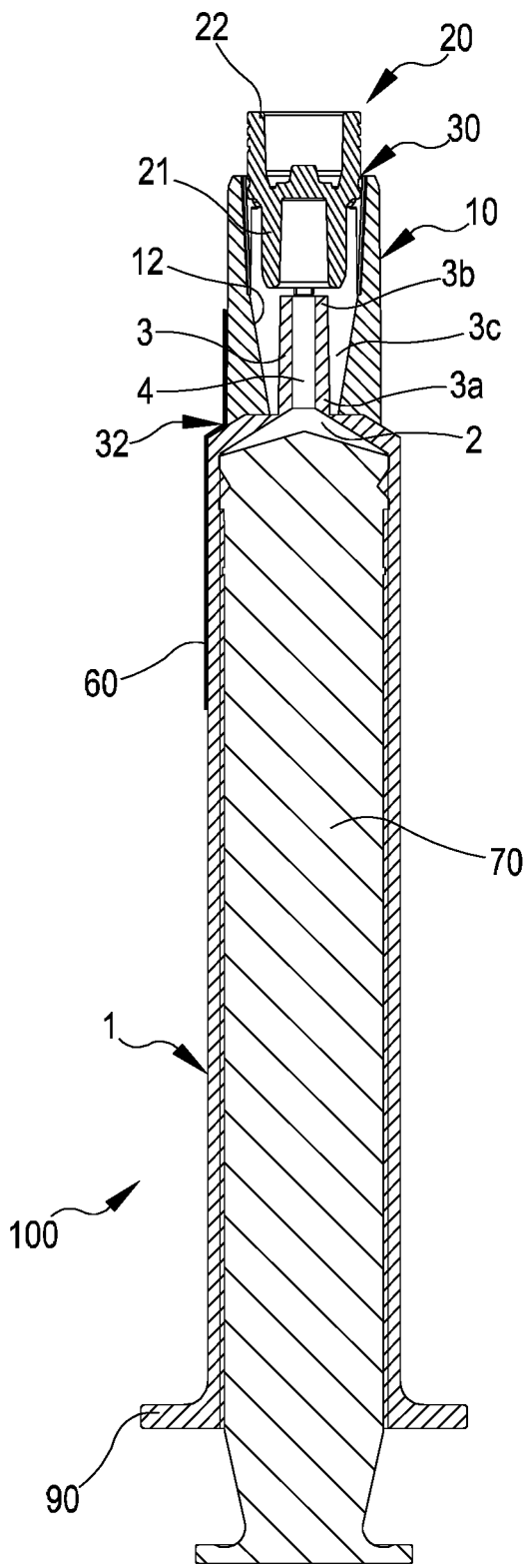
FIGS. 9 and 10 are sectional views of a device in accordance with an alternative embodiment wherein the tip cap is arranged respectively in a first and in a second position.
Figure 10:
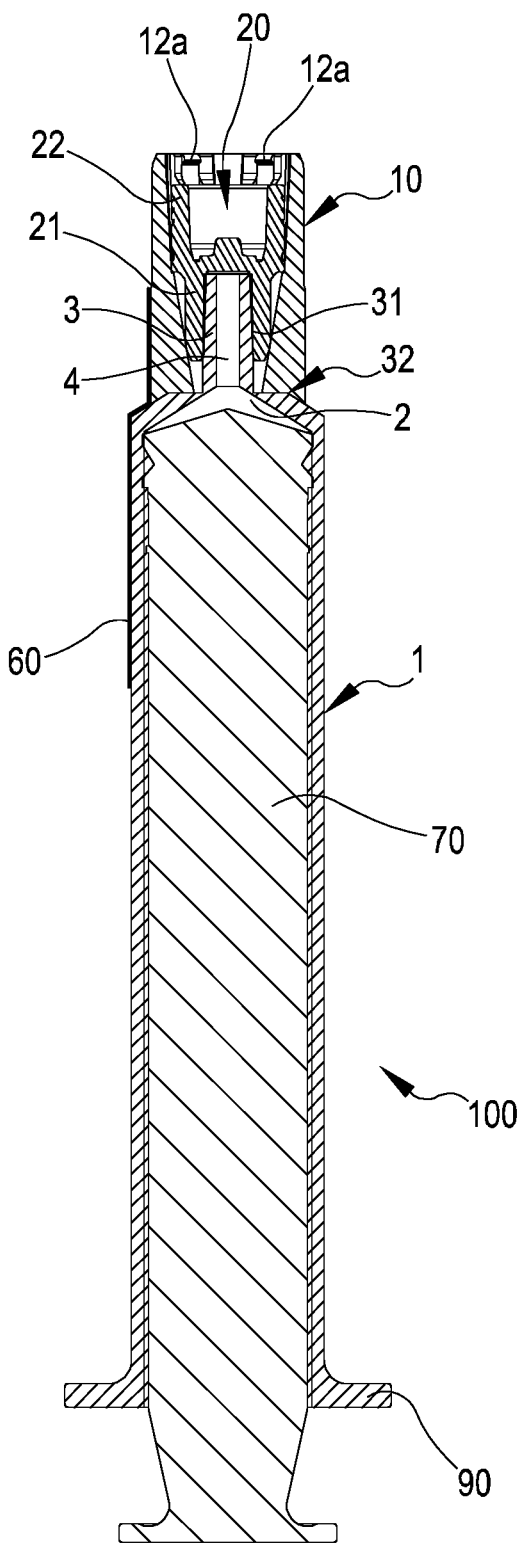

Reference number 100 indicates a device, shown in FIGS. 1 to 5 and further in FIGS. 9 and 10, for medical or laboratory use. The device 100 is adapted to store a fluid, with the purpose of a subsequent selective delivery. In particular, the device 100 can be a syringe, which can be in different sizes and capacities, suited for storing fluid for medical use, in particular a pharmaceutic. The device can be made of plastic material, preferably non-toxic, pyrogen-free and transparent. Alternatively, the device can be made of metallic material, such as for example stainless steel, or in glass.

Figure 1:
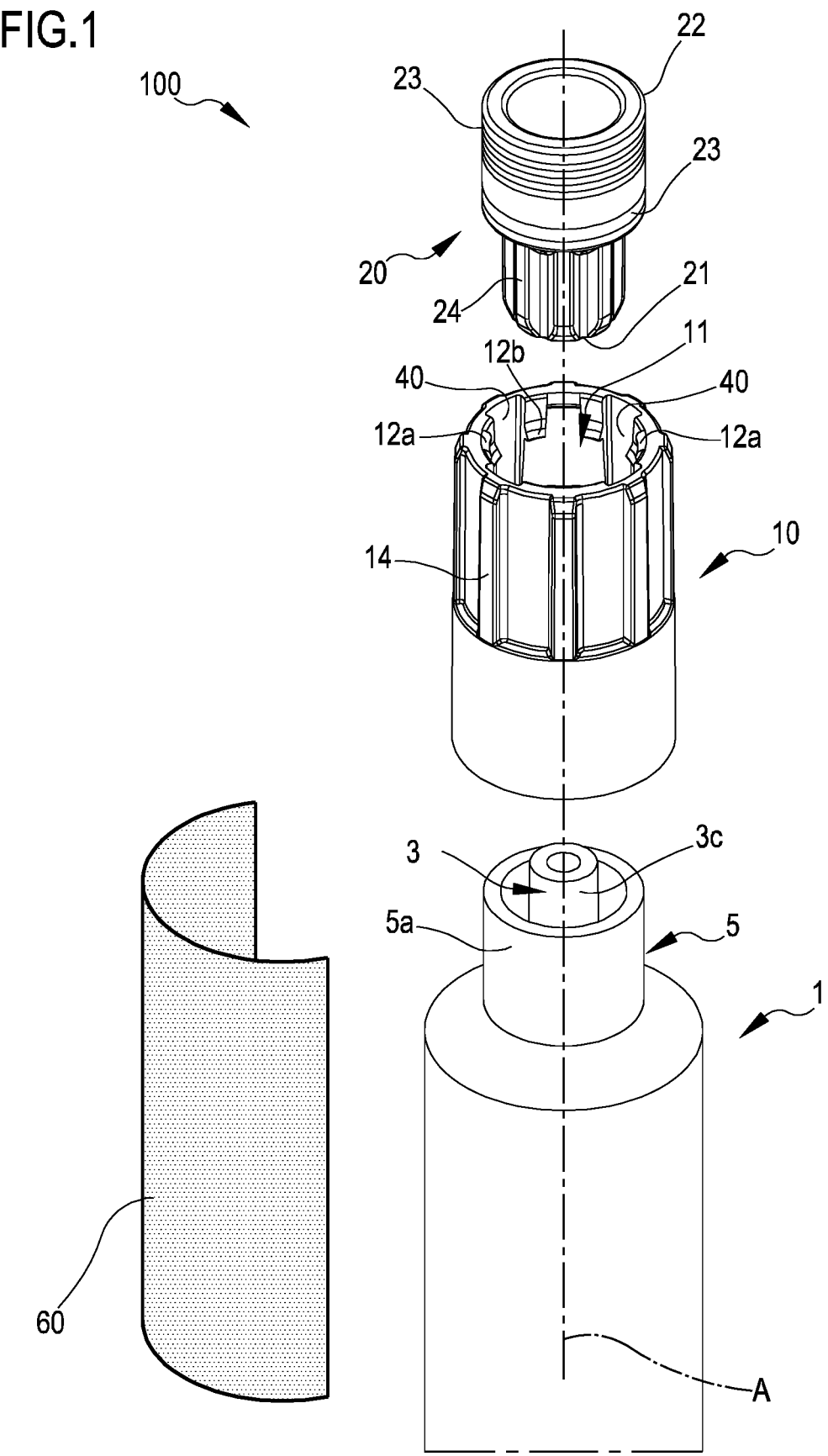
FIG. 1 is an exploded view drawing of a device in accordance with the present invention.
Figures 2, 3:
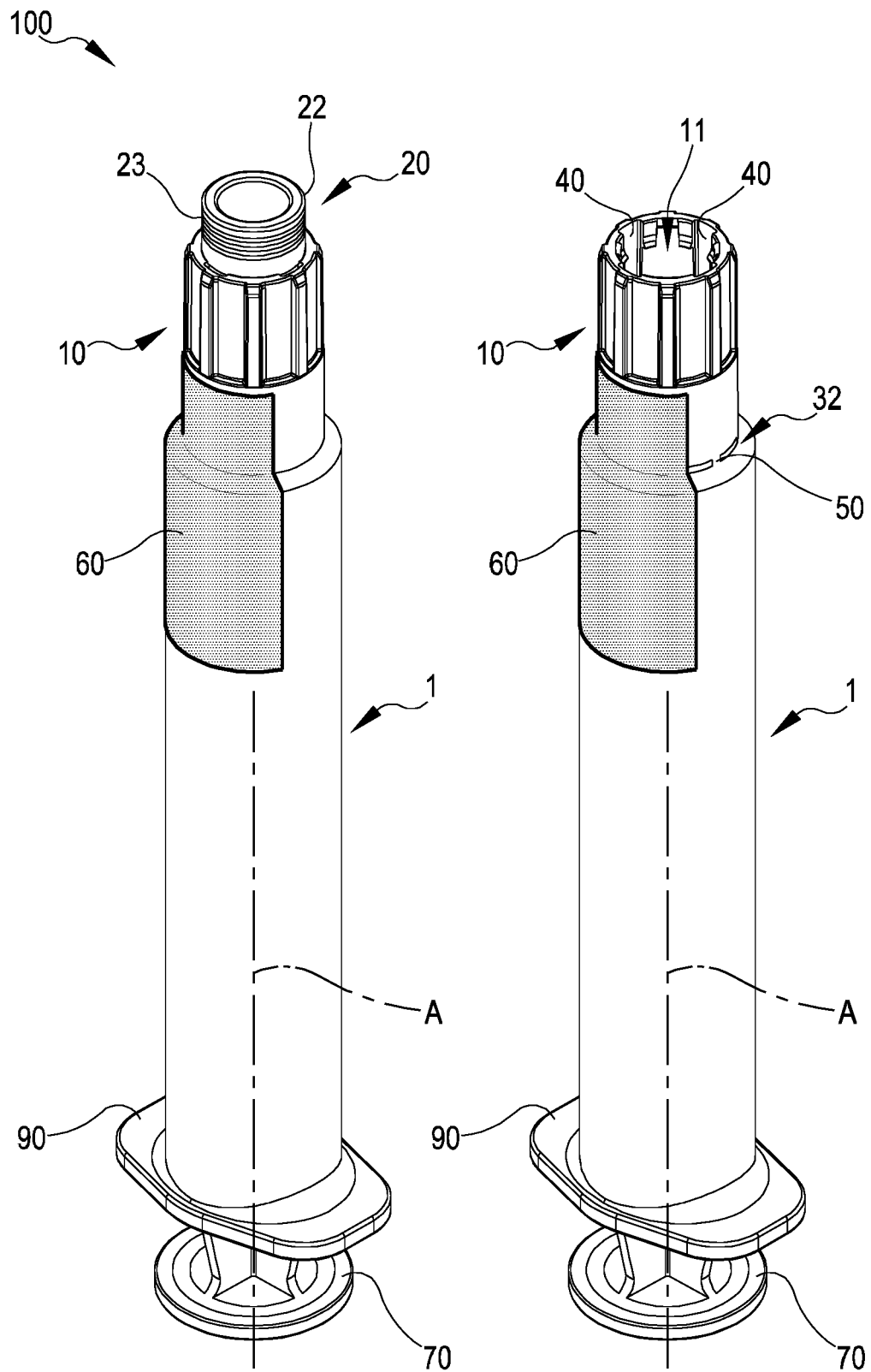
FIG. 2 is a perspective view of a device in accordance with one embodiment in accordance with the present invention.
FIG. 3 is a perspective view of a device in accordance with a further embodiment in accordance with the present invention.

The device 100 comprises a body 1 of axisymmetric shape, with respect to an axis of symmetry A shown in FIG. 2, preferably cylindrical, defining a containment volume 2 within, suited for storing the medical fluid. The body extends between a first and a second end, wherein lobed portions 90 are joined at the first end, in particular a pair of gripping tabs, as shown in FIGS. 1 to 3, which substantially protrude orthogonally with respect to the axis A allowing a user to grip the device 100 and its consequent use. The lobed portions emerge from the body 1 along a main development axis substantially perpendicular to the axis A of the body 1. A plane passing through the axis A and the main development axis represents a plane of symmetry of the device 100.

Advantageously, a graduated scale is applied to the body 1, in order to read the quantity of fluid stored in the containment volume 2.

The device has a length between 30 and 300 mm, more specifically between 70 and 180 mm, and a containment volume capacity between 1 and 200 ml, more specifically between 4 and 60 ml, in particular nominally equal to 5 ml or to 10 ml or to 20 ml or to 50 ml. These dimensions and volumetric capacities of the device 100 are to be considered as an example only: nothing prevents the realization of devices 100 with dimensions and volumetric capacities being larger and smaller than those indicated.

At the second end, the body 1 comprises a terminal 3, shown in the exploded view of FIG. 1 and in the sections of FIGS. 4, 5 and 9, 10, defining a duct 4 configured to put in communication the containment volume 2 with the outside. In other words, the terminal 3 is designed to allow the fixing of an auxiliary accessory (not shown in the attached figures), such as for example a needle or a transfer conduit, which can be fluid-tightly sealed to terminal 3. Terminal 3 has a substantially conical shape extending between a first end 3*a*, engaged to the body 1 of the device and having a first diameter, and a second end 3*b*, free and spaced from the first end 3*a*, wherein the second end 3*b* has a second diameter smaller than the first diameter. In more detail, the terminal 3 is in particular a male Luer connector, having a shape and size in accordance with the current legislation. By way of example, the terminal 3 has a taper angle between 2° and 5°, in particular equal to 3.44°, a length between 5 and 15 mm, in particular equal to 8.4 mm, a first diameter between 4 and 5 mm, in particular equal to 4.42 mm, a second diameter between 3 and 4.5 mm, in particular equal to 4.021 mm, an internal diameter of the duct 4 comprised between 1 and 4 mm, in particular equal to 2.1 mm. The terminal 3 and the body 1 are obtained in a seamless single piece and the body 1 and the terminal 3 can be mutually coaxial.

The body 1 can comprise a collar 5 emerging from the second end of the body 1. The collar 5, shown in the exploded view of FIG. 1, surrounds the terminal 3 and has a cylindrical shape: in particular the collar 5 extends from the body 1 for a shorter length than that of the terminal 3. The collar 5 extends in thickness between an outer lateral surface 5a and an inner side surface, wherein the inner side surface has a threaded coupling which allows the fastening of the auxiliary accessory, in particular the needle or the transfer conduit. In an alternative embodiment shown in FIGS. 9 and 10, the device 100 does not include any collar 5.

The device further comprises a plunger 70 fluid-tightly inserted in the body 1 to define a closing portion of the containment volume 2, and wherein the plunger 70 is movable along the axis A of the body 1 in order to vary the capacity of the containment volume 2.

The device 100 further comprises a cap support 10 integral with the body 1 and arranged externally to the containing volume 2: the cap support 10 substantially has a preferentially cylindrical axisym metric shape and extends from the second end of the body 1. As shown in FIGS. 2 to 5, the cap support 10 completely surrounds the terminal 3 and, if present, the collar 5: in particular the terminal 3 is completely imbedded in an internal volume 11 of the cap support 10. The cap support 10 has a length, measured along the axis A, between 10 and 60 mm, in particular between 15 and 25 mm, and a maximum diameter between 6 and 30 mm, in particular between 10 and 20 mm.

In the figures accompanying the present description, it can be noticed that the maximum diameter of the cap support 10 is minor than the maximum diameter of the body 1 of the device 100. However, it is intended to specify that the present invention is not limited in this sense at all, since any different relation can exist between the aforesaid maximum diameters. In particular, a possible embodiment of the present invention provides that the cap support 10 is sized so as to be substantially flush with the body 1.

The cap support 10 is preferably made of the same material constituting the body 1, preferably plastic (conveniently aseptic and/or pyrogen-free and/or transparent), metal or glass. As evident from the accompanying drawings, an embodiment provides that the radial dimension of the cap support 10 is lower than a radial dimension of the body 1, defining in fact a tapered portion of the device 100. Alternative embodiments are also possible, e.g. an alternative embodiment wherein the radial dimension of the cap support 10 substantially correspond to the radial dimension of the body 1.

The cap support 10 is secured to the body 1 by constraint means 32 configured to engage the cap support 10 to the body 1 in a releasable manner: for this reason the constraint means 32 between the cap support 10 and the body 1 may include an undercut defined between the cap support 10 and the body 1, for example an interlocking coupling between the body 1 and the cap support 10 or between the collar 5 and the cap support 10. Alternatively, the constraint means 32 between the cap support 10 and the body 1 can comprise an interference coupling, for example a friction coupling (as shown in the sectional views of FIGS. 4 and 5) between the outer surface 5a of the collar 5 and an inner surface 12 of the cap support 10: in this case the cap support 10 has a slightly smaller internal diameter with respect to the external diameter of the collar 5 such as to guarantee an interference coupling. The difference between the diameters is such that, given the elastic characteristics of the materials constituting the collar 5 and the cap support 10 respectively, it is possible, by means of appropriate external actions, to make the collar 5 in any case insertable at least partially into the cap support 10. Alternatively or in addition, the constraint means 32 between the cap support 10 and the body 1 comprise a gluing or a welding between the cap support 10 and the body 1 or between the cap support 10 and the collar 5. In a further embodiment, the constraint means between the cap support 10 and the body 1 comprise one or more seals 50 connecting the cap support 10 and the body 1 (as shown in FIG. 3), such that the body 1 and the cap support 10 are joined together seamlessly. The seals 50 define local connections between the body 1 and the cap support 10. In particular, the seals 50 can be realized by means of spot welding between the cap support 10 and the body 1 of the device 100.

In a further embodiment of the present invention, the cap support 10 is obtained in one piece with the body 1, in particular through the same molding operation if in plastic material, the interface between the cap support 10 and the body 1 being defined by means of a weakening line (obtained for example through a sudden reduction in thickness).

Figure 8:
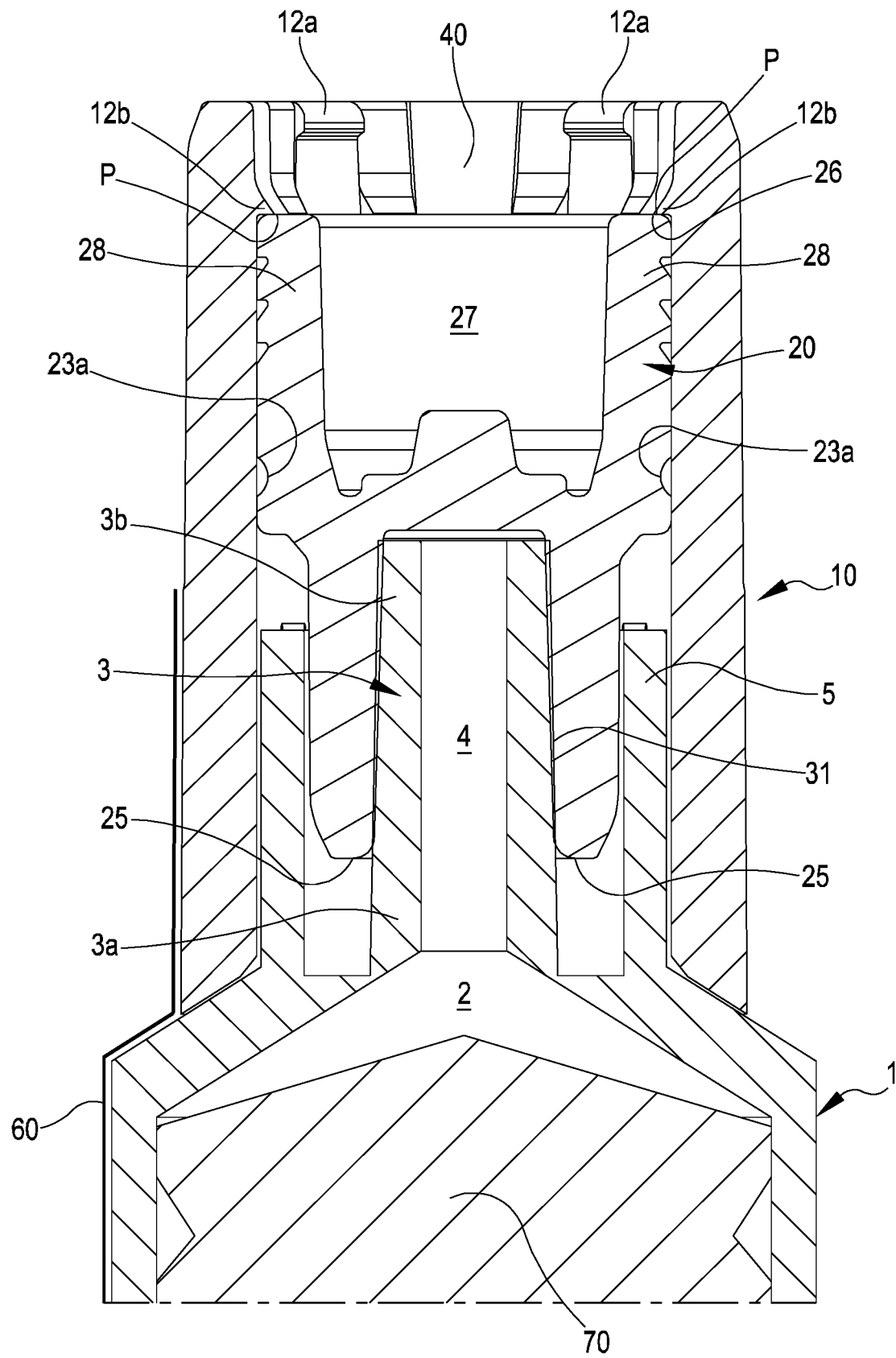
FIG. 8 is a detailed perspective view of a portion of the device in accordance with the present invention.

A further embodiment provides that the cap support 10 is secured to the body 1 by means of sticking an adhesive label 60, shown in FIGS. 1 to 5 and further in FIGS. 8 to 10, at the turn of the cap support and the body of the device. The label, made of paper or plastic, can be an information label, for example having codes or colors representative of the fluid stored in the device. Advantageously, the label can be made with thermal paper, in order to allow printing by means of exposure to a heat source. Alternatively or in addition to the label 60, a sheath (not shown in the attached figures) of heat-shrinkable material can be used, suitable for tightening the cap support 10 and the body 1. In case of joint use of the label and the sheath, the label 60 is applied over the sheath.

In accordance with what has just been described, the cap support 10 can be fastened to the body 1 or to the collar 5 of the body 1 by means of only one or by a combination of the technical solutions proposed above with regard to the third constraint means 32.

Figure 6:
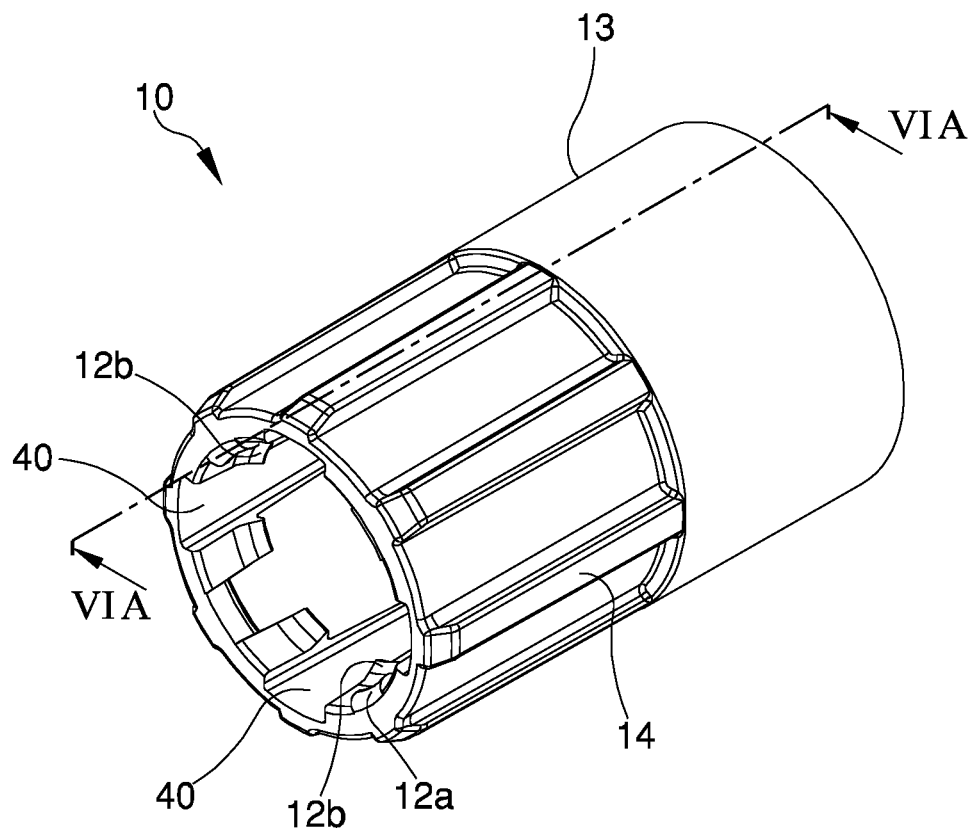
FIG. 6 is a perspective view of the cap support of the device in accordance with a preferred embodiment of the present invention.
Figure 6A:
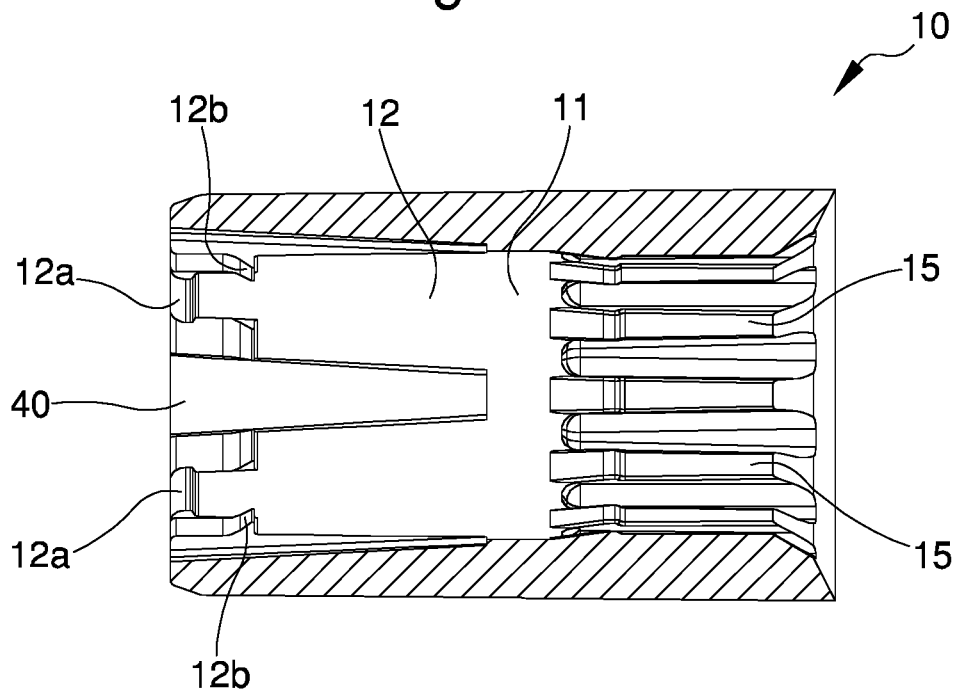
FIG. 6A is a sectional view of FIG. 6.

The cap support 10, in accordance with a preferential embodiment shown in FIGS. 6 and 6A, comprises a plurality of ribs 15 emerging from the inner side surface 12 of the cap support 10 and arranged in the inner volume 11 of the cap support itself. The ribs 15 are joined by interference coupling with an outer lateral surface 5a of the collar 5, defining at least part of the constraining means 32 between the cap support 10 and the body 1. The ribs 15 are equally spaced apart and, if from the outer lateral surface 5a of the collar 5 counter-ribs emerge, they are advantageously suitable for creating a repeatable constraint cooperating with these counter-ribs.

The ribs 15 are apt to make stable and reliable the coupling between the cap support 10 and the collar 5. In fact, both the outer lateral surface 5a of the collar 5 and the inner side surface 12 of the cap support 10 are theoretically cylindrical surfaces, so even minimal deviations from this theoretically cylindrical development (even only due to dimensional tolerances) can compromise a correct and repeatable coupling between the cap support 10 and the collar 5. The ribs 15 emerging from the inner side surface 12 of the cap support 10 (or equivalently similar ribs emerging from the outer lateral surface 5a of the collar 5) allow a better controlled coupling between the cap support 10 and the collar 5, providing that it extends along predefined portions of the surfaces contacting one another, i.e. the outer lateral surface 5a of the collar 5 and the inner lateral surface 12 of the cap support 10.

The ribs 15 can extend towards the inner volume 11 of the cap support 10 along a straight, curved or helical path. The embodiment represented in the figures provides by way of example but not in a limited manner a number of ribs 15 equal to twelve.

The constraint means 32 between the cap support 10 and the body 1 can also include a weakening portion placed between the cap support 10 and the body 1 configured for, at least after an external tearing and/or twisting action exerted on said cap support 10, being damaged or broken to allow a condition of separation of the cap support 10 from the body 1 of the device. Such separation allows to highlight a tampering with the device 100 itself, inhibiting further engagement between the cap support 10 and the body 1 subsequently to said tampering.

In an advantageous embodiment of the present invention, the label 60 can have a weakening portion, placed between the cap support 10 and the body 1, configured to be damaged or broken as a result of such tampering, and allow the separation of the cap support 10 from body 1, thereby highlighting the tampering with the device. Likewise, the seals 50 can also define a weakening portion configured to allow the separation of the cap support 10 from the body 1, highlighting tampering with the device.

The aforesaid weakening portion also allows a user to easily remove the cap support 10, necessary for the use of the device 100 for medical or laboratory purposes. In order to allow or facilitate the grasping of the cap support 10 by a user and the consequent removal of the cap support 10 from the body 1, the cap support 10 comprises, in correspondence with its own outer lateral surface 13, a plurality of gripping projections 14, as shown in FIG. 6. Said projections can advantageously develop longitudinally or transversely with respect to the axis A of the body 1, or define a knurling of the outer lateral surface 13 of the cap support 10 suited to improve the grip.

Figure 7:
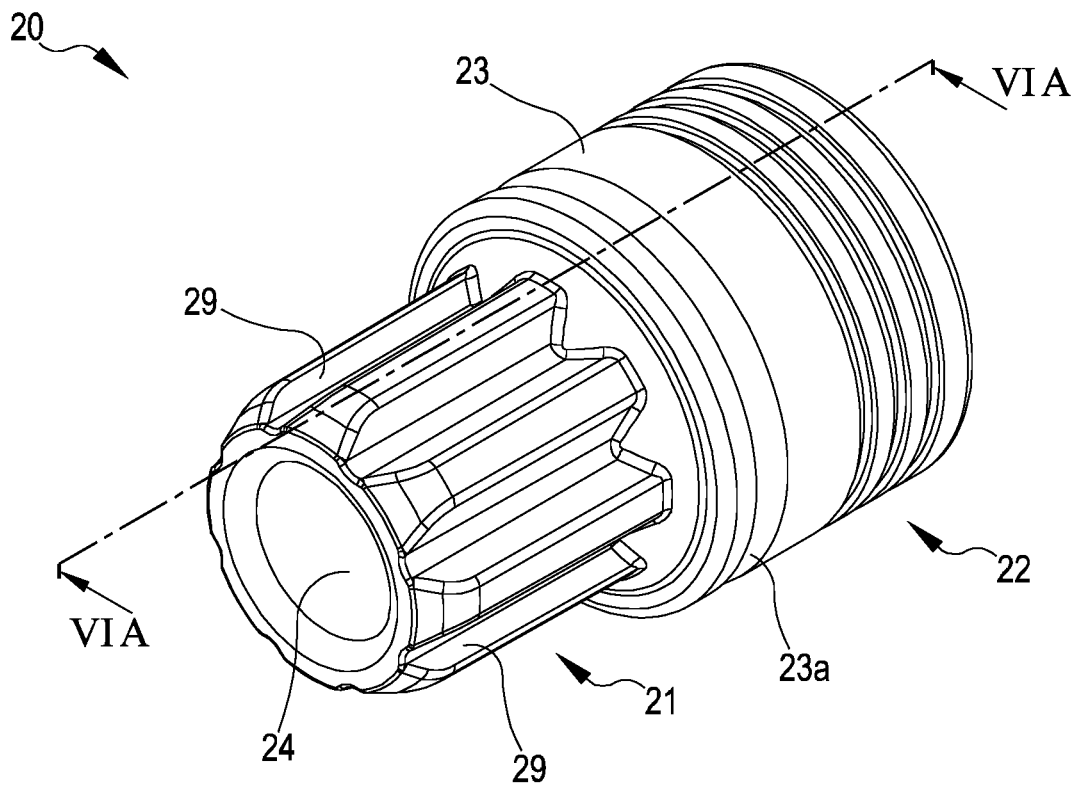
FIG. 7 is a perspective view of the tip cap of the device in accordance with a preferred embodiment of the present invention.
Figure 7A:
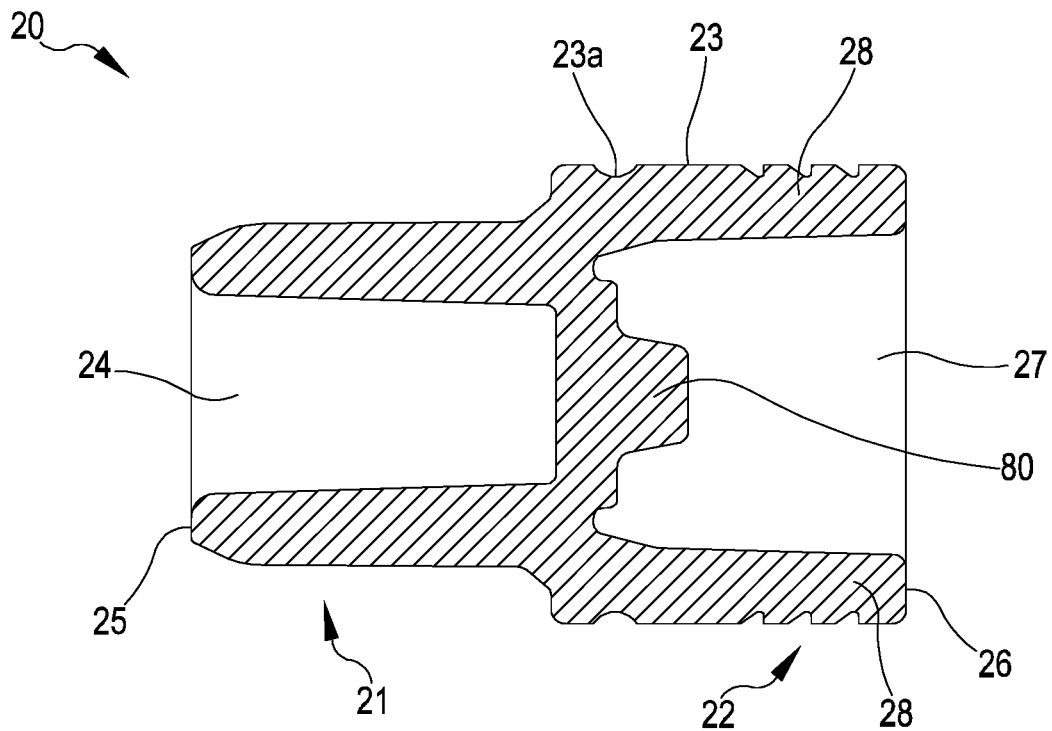
FIG. 7A is a sectional view of FIG. 7.

The device 100 further comprises a tip cap 20, shown in detail in FIG. 7 and in FIG. 7a, associable with the cap support 10 by means of first constraint means 30 and associable with the terminal 3 by means of second constraint means 31. The tip cap 20 has substantially an axisymmetric shape, extending in length with a size from 10 to 40 mm, more particularly from 10 to 20 mm, and having a maximum radial dimension, in particular a diameter, between 4 to 25 mm, more particularly between 7 and 15 mm.

As shown in the attached figures, the preferential embodiment of the device 100 includes the body 1, the terminal 3, the cap support 10 and the tip cap 20 arranged coaxially with each other.

Figure 4:
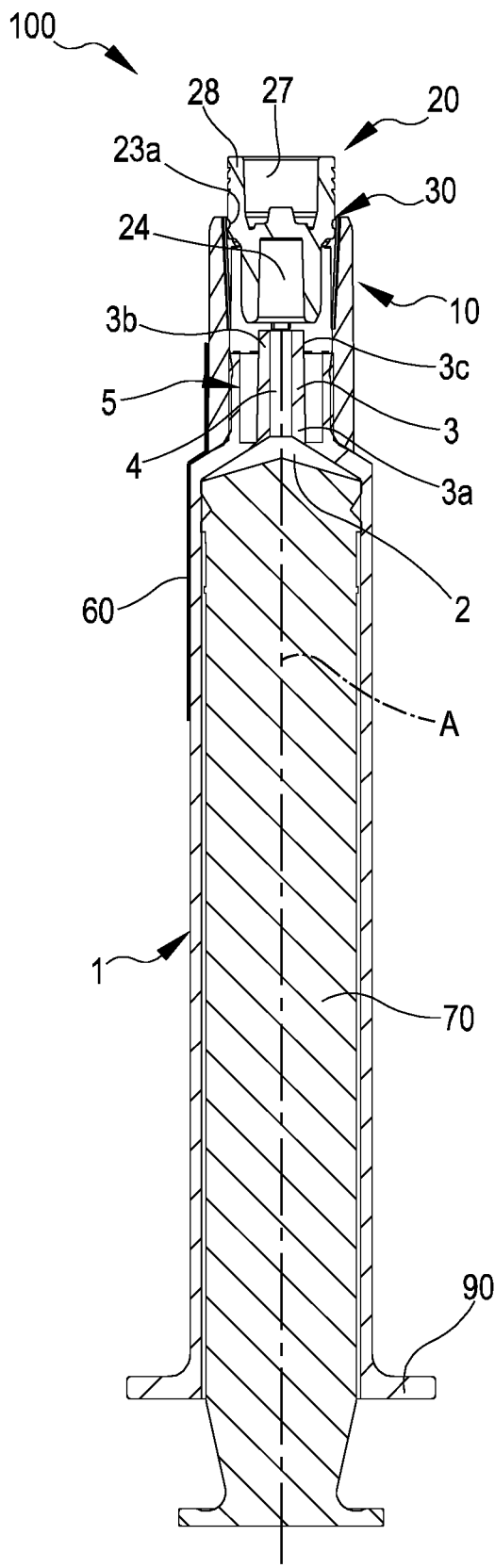
FIG. 4 is a sectional view of a device in accordance with the present invention wherein the tip cap is arranged in a first stable position.

In a first stable position, shown in FIGS. 4 and 9, the tip cap 20 is integral with the cap support 10 by means of the first constraining means, so that a first portion 21 of the tip cap 20 is housed in the internal volume 11 of cap support 10 and a second portion 22 of the tip cap 20 emerges externally from the internal volume 11 of the cap support 10. The first constraint means 30 define a releasable coupling between an inner side surface 12 of the cap support 10 and an outer lateral surface 23 of the tip cap 20, by means of an undercut or, even in combination, an interference coupling, in particular a forced frictional coupling, between the tip cap 20 and the cap support 10. Releasable coupling indicates a constraint wherein the tip cap 20 is stably integral with the cap support 10 with regard to its position along the axis of symmetry (indeed rotation of the tip cap 20 with respect to its axis is however permitted), until an external force intervenes in pushing, pulling or twisting to remove it from this position. In more detail, the first constraint means 30 comprise a circumferential groove 23a formed on the outer lateral surface 23 of the tip cap 20, and one or more reliefs 12a emerging from the inner side surface 12 of the cap support 10 towards the internal volume 11 of the cap support 10. The reliefs 12a are configured to fit into the circumferential groove 23a when the tip cap 20 is in the first stable position, defining an undercut which guarantees the connection between the cap support 10 and the tip cap 20 and consequently the retention of the first stable position. FIGS. 4 and 9 show the tip cap 20 arranged in the first position, wherein the coupling between the tip cap 20 and the cap support 10 can be noticed, so that the circumferential groove 23a cooperates with the reliefs 12a emerging from the cap support 10. In an alternative embodiment (not shown in the attached drawings), the circumferential groove can be obtained on the inner side surface 12 of the cap support 10 and the reliefs 12a emerge from the outer lateral surface 23 of the tip cap 20.

When the tip cap 20 is in the first stable position, the containment volume 2 is in fluid communication with the outside by means of recesses 40, shown in detail in FIG. 6 and in FIG. 6A, obtained on the outer lateral surface 23 of the tip cap 20 and/or on the inner side surface 12 of the cap support 10 and defining a plurality of gaps between the cap support 10 and the tip cap 20. The recesses 40 are preferably angularly equally spaced apart and develop along a rectilinear path (along substantially parallel directions to the axis of symmetry A or with an angle of incidence with respect to the axis of symmetry A), or along a curved path or along a helical path. The recesses 40 may extend along the entire extension of the cap support 10 or of the tip cap 20. Alternatively, the extension of the recesses 40 may be limited (as shown in the attached figures) to a specific portion of the cap support 10 or of the tip cap 20.

In other words, as evident from the sectional views in FIGS. 4 and 9, the containment volume 2, when the tip cap 20 is in the first stable position, is in communication with the internal volume 11 of the cap support 10 by means of the conduit 4 of the terminal 3. Being the containment volume 2 in fluid communication with the outside, the first stable position allows the passage of a sterilizing and/or sanitizing gas from the outside towards the containment volume 2, so as to determine a sterilization of the device 100, and at the same time keep the tip cap 20 integral with the device 100.

Figure 5:
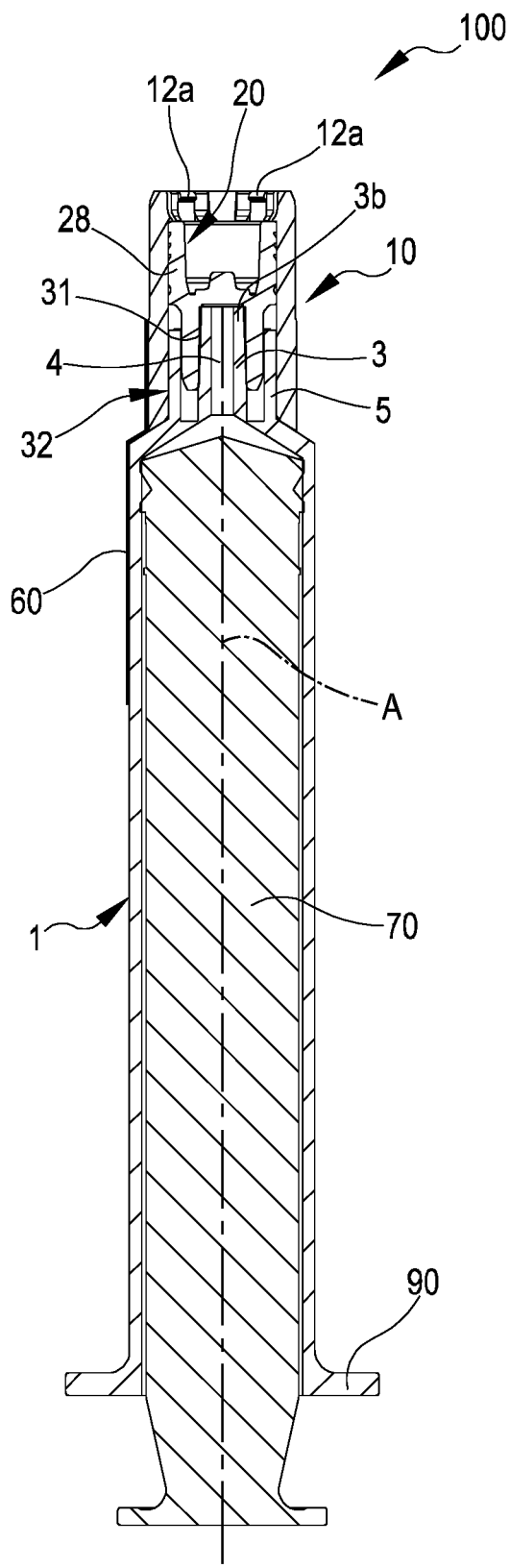
FIG. 5 is a sectional view of a device in accordance with the present invention wherein the tip cap is arranged in a second stable position.

As previously indicated, the first constraint means 30 define a releasable coupling to allow the tip cap to be arranged in a second stable position, shown in FIGS. 5, 8 and 10, wherein the tip cap 20 is integral with the terminal 3 by means of the second means of constraint and completely housed in the internal volume 11 of the cap support 10. When the tip cap 20 is in the second stable position, the containment volume 2 is fluid-tightly sealed. This allows, after the sterilization phase (previously carried out, i.e. when the tip cap 20 is arranged in the first stable position), to maintain the containment volume 2 of the device 100 sterile.

In the second stable position, the tip cap 20 is in contact with the terminal 3. In particular, the tip cap 20 comprises a blind internal cavity 24, shown in detail in FIGS. 7 and 7A, configured to receive by insertion, when the tip cap 20 is in the second stable position, at least one end portion of the terminal 3 to determine a fluid-tight closing between the external environment and the containment volume 2. The blind cavity 24 is arranged in correspondence of the first portion 21 of the tip cap 20 and oriented towards the terminal 3. Furthermore, the cavity 24 can also have a conical shape complementary to the terminal 3 such as to define a stable conical coupling with the terminal 3 and improve the fluid tight seal.

When the tip cap 20 is arranged in the second stable position, an end portion 25 of the first portion 21 is pressure bound between an outer lateral surface 3c of the terminal 3 and an inner surface of the collar 5, as shown in the sectional view of FIG. 8.

Such pressure is rather effective in countering (even in preventing) a possible attempt to remove the tip cap 20 from its second stable position. Moreover, this pressure determines an elastic deformation of the collar 5 in a radial direction, this deformation transmitting to the portion of the cap support 10 which encloses the collar 5, so that this portion of the cap support 10 consecutively deforms elastically in a radial direction. The deformations and subsequent tensions that are created in the radial direction effectively counteract possible actions in the axial direction on the tip cap 20 and on the cap support 10, for the benefit of the safety and reliability of the setting of the tip cap 20 in the second stable position.

In the embodiment providing for the absence of the collar 5, the end portion 25 of the first portion 21 is pressure bound between the outer lateral surface 3c of the terminal 3 and the inner lateral surface 12 of the cap support 10, as shown in FIG. 10. In this regard, said embodiment can provide for a tapered inner surface 12 of the cap support 10. The sectional views in FIGS. 9 and 10 show in fact that the inner surface 12 of the cap support 10 is advantageously inclined, so as to allow the end portion 25 of the first portion 21 of the tip cap 20, when arranged in the second stable position, to be press-fitted stably between the terminal 3 and the cap support 10.

The tip cap 20 may further comprise one or more ribs 29 arranged in relief on the outer lateral surface 23 of the tip cap 20 in correspondence of the end portion 25 of the first portion 21. The ribs 29 are apt to be bound to the inner surface 12 of the cap support 10 or to the inner surface of the collar 5 when the tip cap 20 is in the second stable position (see FIGS. 5, 8 and 10) and they are configured to be deformed by squashing so as to allow the tip cap 20 to be stably constrained in its own second stable position. It should be noted that, if the inner surface of the collar 5 has a tapping, for example a threading, the ribs 29 are configured to deform and cooperate with the tapping and determine a further constraint capable of preventing a removal of the tip cap 20 from the second stable position.

What stated above in regard to the presence of one or more ribs 29 is to be considered as merely representative of one possible embodiment of the present invention, since a different embodiment can alternately exist, according to which ribs are not provided on the end portion 25 of the first portion 21 of the tip cap 20.

The device further comprises auxiliary constraint means configured to inhibit or counteract the transition of the tip cap 20 from the second to the first stable position. Advantageously, the auxiliary constraint means include projections 12b, shown in FIGS. 6, 6A and 8, emerging from the inner surface of the cap support 10 and arranged in the internal volume 11 of the cap support 10, these projections 12b being configured to allow the insertion of the tip cap 20 in the inner volume 11 of the cap support 10 and the transition of the tip cap 20 from the first to the second stable position.

Furthermore, the projections 12b are configured to make very difficult the extraction of the tip cap 20 (when in the second stable position) from the internal volume 11 of the cap support 10 and therefore decisively hamper the transition of the tip cap 20 from the second to the first stable position.

As evident from the sectional view of FIG. 8, when the tip cap 20 is disposed in the second stable position, an end portion 26 of the second portion 22 of the tip cap 20 abuts against a barrier plan defined by the projections 12b of the auxiliary constraint means 33, wherein the barrier plan inhibits or counteracts the transition of the tip cap 20 from the second to the first stable position. In other words, the barrier plan defined by the projections 12b inhibits or counteracts the axial movement of the tip cap 20 along the axis A away from the terminal 3.

In constructive terms, the different behavior of the projections 12b is due to the fact that the tip cap 20, in the transition from the first to the second stable position, encounters a gentle and gradual ramp that the tip cap 20 easily manages to overcome by deforming elastically and thus reducing its external diameter, while in the transition from the second to the first stable position it encounters an abrupt variation of section in the form of a step which causes the tip cap 20 to stop sliding.

In a preferential embodiment, the projections 12b and the reliefs 12a emerge from the inner lateral surface 12 of the cap support 10 and are interposed between successive recesses 40 according to a repeated angular pattern. As an example provided merely for explanatory but not limitative purposes, this repeated angular pattern may provide that, progressively, a first projection, a relief and a second projection are interposed between one recess and the following one. Thus providing for a number of recesses 40 equal to four, it occurs that, according to this non-limiting example, the number of reliefs 12a is also equal to four, while the number of the projections 12b is equal to eight.

The second end portion 26 of the tip cap 20 has a slightly larger diameter than the inner diameter of the cap support 10, defining an interference coupling in order to improve the seal. The difference between the diameters is such that, given the elastic characteristics of the materials constituting the tip cap 20 and the cap support 10 respectively, it is possible, by means of appropriate external actions, to make the tip cap 20 in any case insertable at least partially inside the cap support 10. In particular, the difference between the maximum diameter of the tip cap 20 and the inner diameter of the cap support 10 is between 0.01 mm and 2 mm, in particular between 0.1 mm and 2 mm, wherein the values of these diameters are measured in a rest condition wherein the tip cap 20 and cap support 10 are separated from each other and are therefore not subject to any elastic deformation.

In a preferential embodiment, the tip cap 20 is made of a material whose elastic modulus is lower than the elastic modulus of the material constituting the cap support 10, in order to facilitate the interference insertion of the tip cap 20 in the internal volume 11 of the cap support 10. In particular, the tip cap 20 is made of elastomeric material, for example rubber or silicone, while the cap support 10 is made of substantially rigid plastic material. This allows to improve the fluid tightness with the terminal 3 in order to isolate the containment volume 2 of the device 100, guarantee an effective seal to counteract the removal of the tip cap from its second stable position, and simultaneously allow easy insertion of the tip cap in the cap support 10. The reduced stiffness in fact allows the tip cap 20 to deform adequately so as to prevent impediments to the transition from the first to the second stable position, and also to act as a gasket when joined to terminal 3 in order to implement the fluid tight seal.

In a further embodiment not shown in the attached figures, the tip cap 20 has a structure, in particular an inner core, made of a first material, and a coating made of a second material, wherein the second material has a lower elastic modulus than the elastic modulus of the first material. The first material can be a plastic, metal or glass, while the second an elastomeric material, for example rubber or silicone.

The second material can be placed, seamlessly or in intervals, on the lateral surface 23, being such lateral surface 23 apt to engage with the inner surface 12 of the cap support 10 for defining the first constraint means 30. In other words, the coating is interposed between the internal core of the tip cap 20 and the inner surface 12 of the cap support 10, in order to define an easily deformable area of the tip cap 20 and therefore allow the correct insertion of the latter inside the cap support 10. Furthermore, the coating can be suitably arranged in correspondence of the blind cavity 24 of the tip cap 20 to define a sealing gasket with the external surface 3c of the terminal 3 in order to improve the tight-fluid seal.

It follows that, alternatively, it can be provided that the tip cap 20 is integrally made of a rigid material and that the coating material with significant elastic properties is applied to the inner surface 12 of the cap support 10 and/or to the external surface 3c of the terminal 3.

Another possible embodiment of the present invention provides that the tip cap 20 and the body 1, in particular the tip cap 20 and the cap support 10, are made of one and the same material, for example a plastic, aseptic, pyrogen-free and transparent material. According to this embodiment, it is possible to provide that applications in soft and/or elastic material are arranged on the surfaces of the tip cap 20 and/or of the cap support 10 and/or of the terminal 3 of the body 1, in order to make the coupling between these elements stronger and more secure and improve the fluid-tight seal.

It has to be noted that, when a user separates the cap support 10 from the body 1, prevailing on the constraint means operating between these elements, the tip cap 20 can remain engaged to the cap support 10, thus also separating from the terminal 3 and determining the opening of the containment volume 2 of the device. Once the user has removed the cap support 10, and then the tip cap, the terminal 3 is accessible from the outside so as to allow the connection of the auxiliary accessory (needle or transfer conduit). As an alternative to this technical solution aimed at maximizing the practicality of the operations required to the user, in order to safeguard as much as possible instead the sterility of the medication stored in the device 100, it can be provided that the separation of the cap support 10 from the body 1 is not sufficient to determine the removal of the tip cap 20, since the latter must be due to a further action subsequent to the separation of the cap support 10.

The tip cap 20 also has a gripping cavity 27, facing outwards and arranged at least partially in correspondence of the second portion 22 of the tip cap 20 itself, configured to receive in thrust a coupling member for determining the passage of the tip cap 20 from the first to the second stable position. In other words, the gripping cavity 27 defines a concavity of the tip cap 20 delimited by perimetric walls 28 emerging from a central portion of the tip cap 20, the latter externally abutting the cap support 10. The presence of this gripping cavity 27 increases the flexibility of the tip cap 20, in particular it allows to define flexible side walls 28, facilitating their coupling with the reliefs 12a and with the projections 12b and consequently facilitating the insertion of the tip cap 20 in the cap support 10 during the transition from the first to the second position.

The tip cap 20 can also have a centering protrusion 80, shown in the sectional view of FIG. 7A, emerging from a bottom portion of the gripping cavity 27, and entirely arranged inside the latter in correspondence of the axis of symmetry A of the tip cap 20.

The geometry of the protrusion 80 is such as to define, around it, an annular surface (well represented in FIG. 7A and in FIG. 8) suited to be used as a thrust surface for this coupling member, so that the thrust force applied on the tip cap 20 is distributed and has a resultant substantially positioned on the axis A, thus avoiding that generate torques and limiting the insertion movement of the tip cap 20 within the cap support 10 exclusively to the action of axial stresses.

In order to avoid that the thrust action by the coupling member can cause undesired deformations of the tip cap 20 (in particular deformations in the axial direction, such that the bottom surface of the cavity 24, deviating from its substantial planarity, is inflected inwards, stopping the insertion of the tip cap 20 before it is due, with negative repercussions of the seal of the tip cap 20 in the second stable position), it is advisable to provide for an adequate thickness of the tip cap 20 in correspondence with the annular thrust surface.

Methods Implementable by Means of the Device

By means of the device 100 described above, in particular because of the capacity of the tip cap 20 to be positioned in the first stable position and in the second stable position described above, it is possible to perform some peculiar procedures.

A first peculiar procedure is a sterilization method of the device 100, wherein the tip cap 20 is arranged in the first stable position in order the sterilization method to be performed.

The device 100, with the tip cap 20 arranged in the first stable position, i.e. in the position wherein the containment volume 2 of the device 100 can communicate with the outside (being a first portion 21 of the tip cap 20 housed in the internal volume 11 of the cap support 10 and a second portion 22 of the tip cap 20 emerging from the internal volume 11 of the cap support 10), is disposed inside a control volume, from which at least part of the gas (in particular air) within can be preliminarily aspirated.

At least one sterilizing gas is then infused into the control volume, so that it can reach the containment volume 2 of the device 100 and thus perform the desired sterilization and/or sanitization of the device 100 which will then be ready to receive the medication. In particular, the transit of the sterilizing gas from the control volume to the containment volume 2 takes place through the recesses 40 intentionally obtained between the outer lateral surface 23 of the tip cap 20 and the inner lateral surface 12 of the cap support 10.

Once the sterilization method has been carried out, the device 100 is packaged, individually or together with other devices equally subjected to sterilization, in a sterile container, in order to allow its transport and preserve its sterility until use, in particular until being filled.

A second peculiar procedure is a filling method of the device 100, during which the tip cap 20 is moved from the first stable position to the second stable position.

The device 100, with the tip cap 20 positioned in the first stable position, i.e. in the position wherein the containment volume 2 of the device 100 can communicate with the outside (being a first portion 21 of the tip cap 20 housed in the internal volume 11 of the cap support 10 and a second portion 22 of the tip cap 20 emerging from the internal volume 11 of the cap support 10), it is processed manually or, according to a preferred alternative, by an automatic filling machine.

In a first phase of the filling method, the tip cap 20 is removed from the device 100. In case of implementation of the method by means of an automatic filling machine, this machine can comprise a bracket with stationing means for the tip cap 20. In particular, the bracket is actuated to move towards and away from the device 100 and the stationing means comprise a pin shaped to engage in the gripping cavity 27 of the tip cap 20. Advantageously, the stationing means can be associated with releasable gripping means (for example a gripper) which facilitate the removal of the tip cap 20 by tightening the perimetral walls 28 of the second portion 22 of the tip cap 20.

In a second phase of the filling method, the terminal 3 of the device 100 (now reachable having the tip cap 20 been removed) is connected tightly with a filling terminal, advantageously in fluid communication with a bag carrying the medication which is intended to fill the containment volume 2 of the device 100. In case of implementation of the method by means of an automatic filling machine, this filling terminal can move towards the device 100, in particular to the terminal 3.

In a third phase of the filling method, a predetermined quantity of fluid, in particular a medication, is transferred, in particular from the bag to the containment volume 2 of the device 100. This transfer can take place by moving the plunger 70 away from the terminal 3 by a measure corresponding to the volume of medication to be transferred. In case of manual implementation of the method, the stroke of the plunger 70 can be adjusted using the graduated scale. If instead the method is implemented by means of an automatic filling machine for which the plunger 70 is moved by appropriate gripping means (for example a gripper) which operate while moving away from the device 100, the stroke of the plunger 70 can instead be regulated by controlling the movement of these gripping means.

In a fourth phase of the filling method, the filling terminal is disconnected from the terminal 3 of the device 100. In case of implementation of the method by means of an automatic filling machine, this filling terminal can move away from the device 100, in particular from terminal 3.

In a fifth and final phase of the filling method, the tip cap 20 is arranged in the second stable position wherein the tip cap 20 fluid-tightly seals the containment volume 2, being integral with the terminal 3 and being completely housed in the internal volume 11 of the cap support 10. In case of implementation of the method by means of an automatic filling machine, this fifth phase can be performed by means of the bracket already used for the first phase of the method, the tip cap 20 being positioned on the stationing means, advantageously resting on the annular surface surrounding the protrusion 80. In particular, the bracket is actuated to move closer to the device 100, until the terminal 3 is inside the blind cavity 24 and the end portion 25 of the first portion 21 of the tip cap 20 is pressure bound between the outer lateral surface 3c of the terminal 3 and to the inner surface of the collar 5, thus getting into the second stable position of the tip cap 20. It should be noted how the second stable position of the tip cap 20, obtained at the end of the filling method, is such an advantageous position that a subsequent removal of the tip cap 20 can only take place by leaving tampering evidence.

Supporting Element and Container

Figure 11:
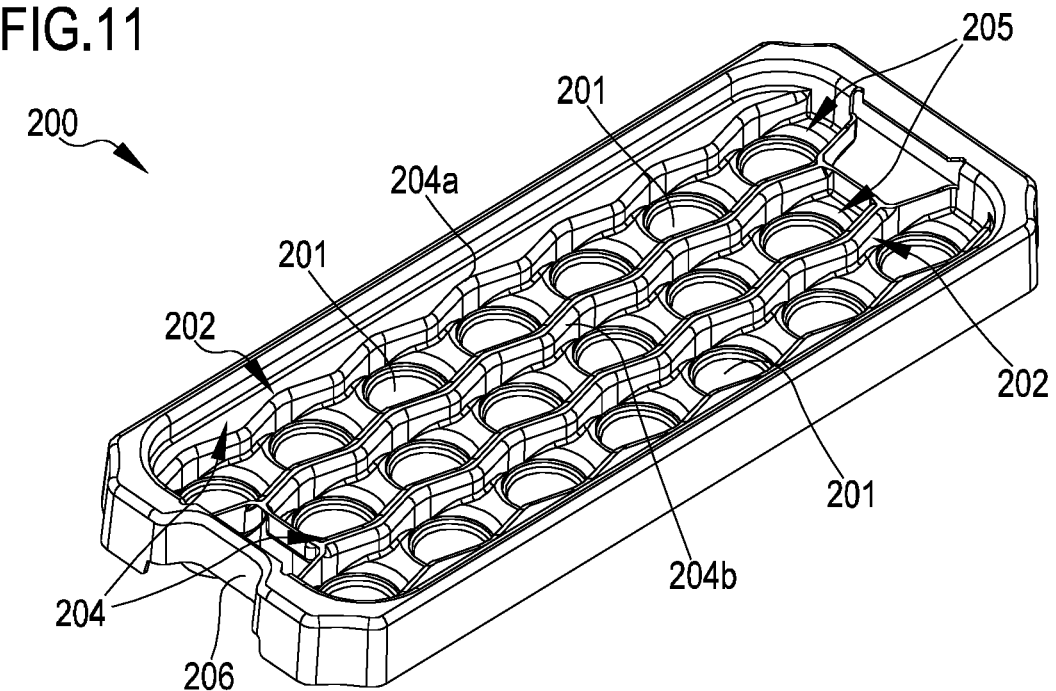
FIG. 11 is a perspective view of a supporting element in accordance with the present invention.
Figure 12:
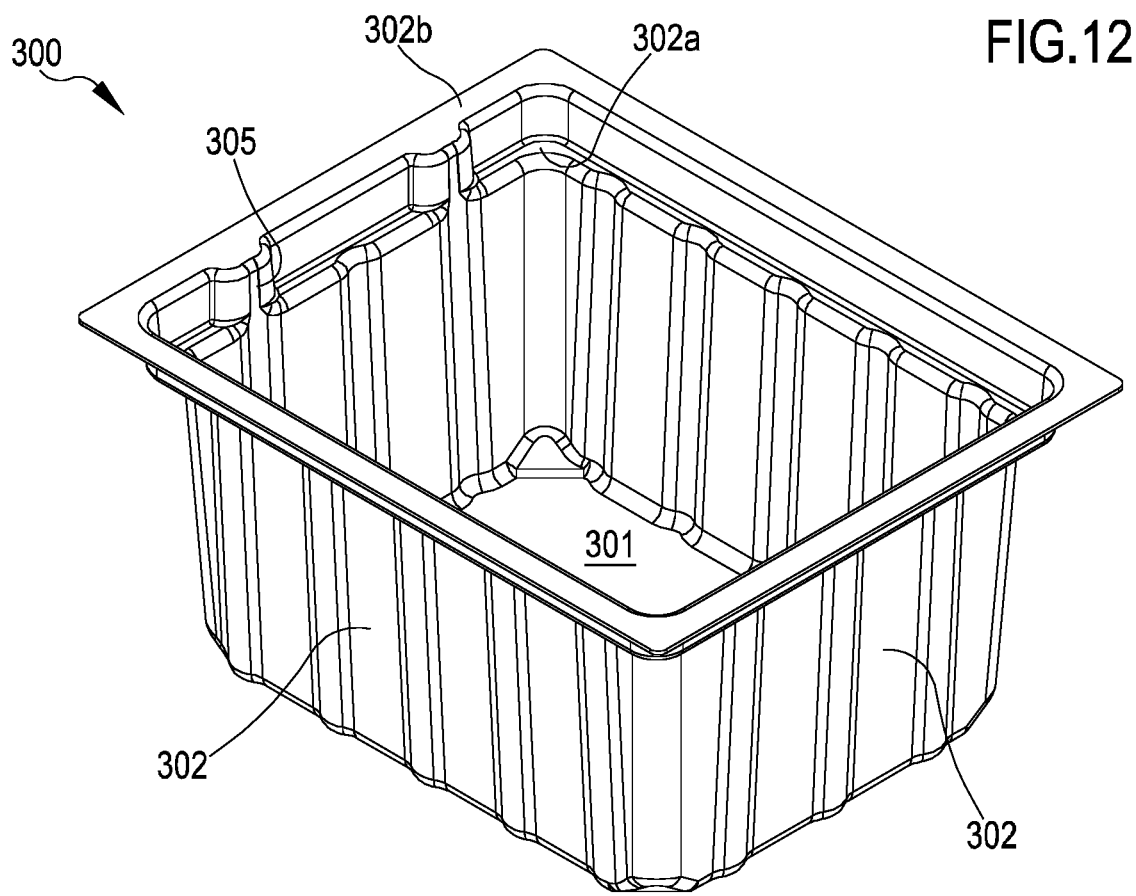
FIG. 12 is a perspective view of a container in accordance with the present invention.
Figure 13:
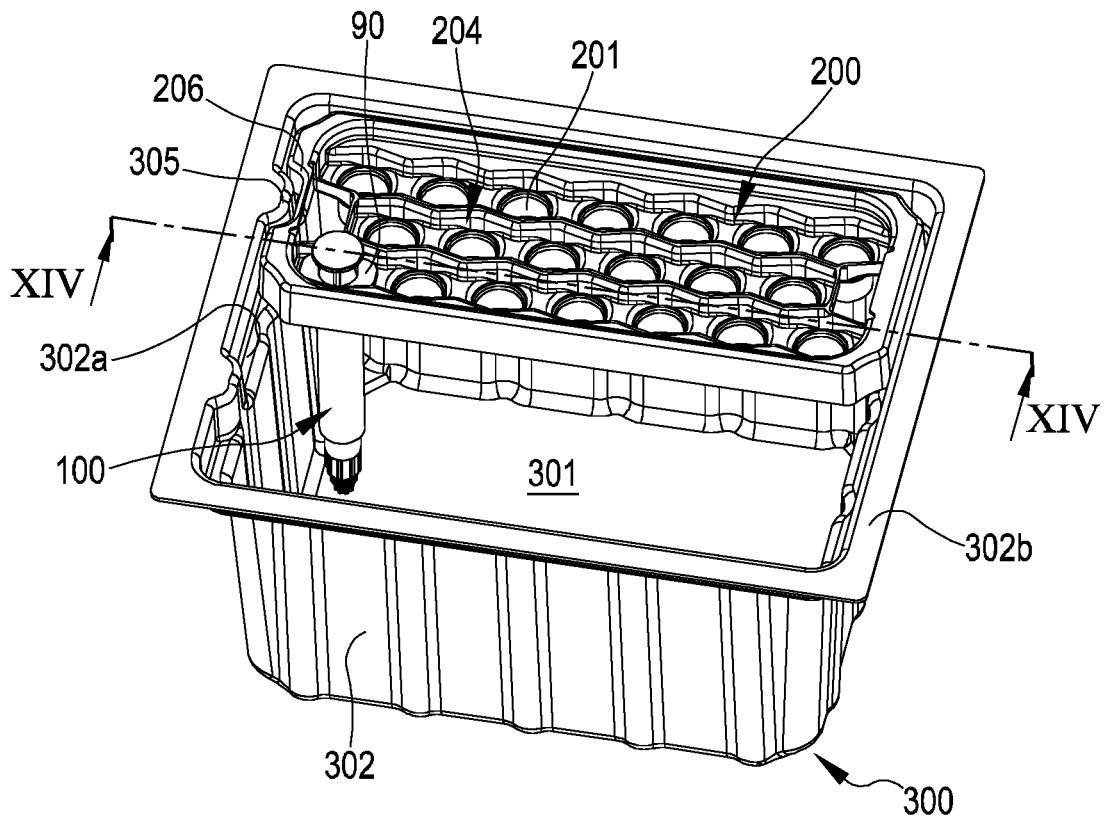
FIGS. 13 and 14 are, respectively, axonometric and sectional views of a supporting element in accordance with the present invention, held onto a container in accordance with the present invention.
Figure 14:
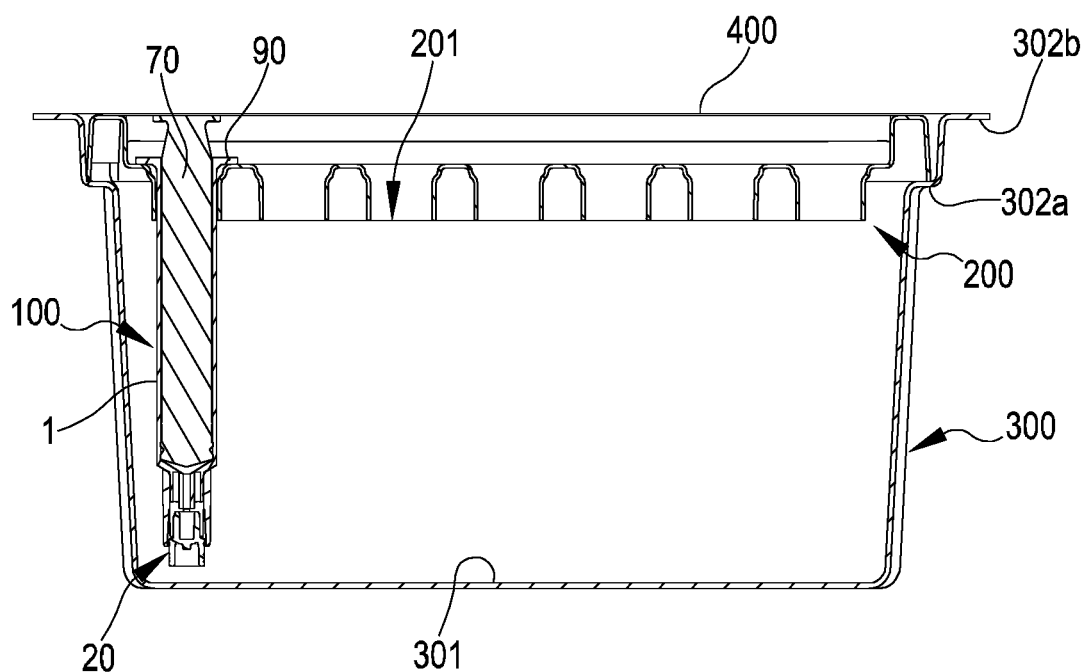

The present invention further relates to a supporting element (one embodiment of this is shown in FIGS. 11, 13 and 14) apt to hold and to support devices, in particular with a cylindrical development, preferably syringes, and a container (one embodiment of this is shown in FIGS. 12 to 14) adapted to carry such devices by receiving such supporting element. In FIGS. 13 and 14, the supporting element and the container are sized so that the container can receive two supporting elements. However, this size is to be considered purely by way of non limiting example, since alternative sizes are possible according to which the container can receive a single supporting element or more than two supporting elements.

It is very important to underline that, although in particular in FIG. 13 the supporting element is represented in combination with a device 100 as previously described, this supporting element can also be used in combination with devices of different types, while maintaining its advantageous features.

The supporting element is configured in the form of a plate 200, preferably rectangular shaped and having through openings 201 sized and shaped to hold a syringe 100 inserted therein. The through openings 201 preferably have a circular shape with a diameter equal to or slightly greater than the syringes to be housed, so that the syringes can fit into these through openings 201. The through openings 201 are arranged along rows side by side, as shown in FIG. 11, wherein each of these rows is substantially parallel to the adjacent one, the openings between two consecutive rows being particularly offset from each other, so as to optimize the load capacity at equal encumbrance.

The supporting element is shaped so as to comprise positioning means 202 suited to allow the syringe 100 to be housed in the through opening 201 exclusively according to two predetermined angular orientations that are out of phase by 180° with each other. In detail, the positioning means 202 define cavities for housing the lobed portions 90 of the syringe 100, the latter being configured to abut a support plane of the supporting element.

The through openings are delimited by side walls 204, in particular from at least a first positioning wall 204a and a second positioning wall 204b, rising from the supporting element and facing each other to define at least part of the positioning means 202. The first positioning wall 204a and the second positioning wall 204b define in combination a groove 205 extending between end portions of the supporting element to define the housing cavities for the syringes. The first positioning wall 204a and the second positioning wall 204b are configured to maintain the correct orientation of the lobed portions 90 of the syringe 100. It is also possible to configure the groove in such a way as to generate embossed sections having, at least in correspondence of each through opening, a shape at least partially complementing the lobed portions of the syringe and consequently to impose a certain angular position. The syringes, when arranged in the openings 201 of the supporting element, have the main development axes of the lobed portions 90 substantially parallel to each other. The side walls 204 extend along a wavy curvilinear path to define the positioning means 202 and the corresponding cavities. The supporting element presents a plurality of grooves 205 adjacent to each other and separated by a wall between said first and second positioning wall.

The container 300 has a bottom 301 and side walls 302 raising from the bottom to define an internal volume. The side walls 302 extend between an attachment portion with the bottom and a free end portion. The container 300 is configured to hold the supporting element in correspondence of the end portion of the side walls. When held by the container, the supporting element remains at a distance from the bottom of the container.

The container 300 includes coupling means configured to allow the reception of the supporting element only at a predetermined position and/or at a predetermined orientation. In the embodiment shown in FIG. 13, the coupling means of the container include at least a protrusion 305 configured to be inserted in a corresponding recess 206 of the supporting element, in order to allow the coupling of the container with the supporting element in a single relative position. The coupling means according to the embodiment shown in FIG. 13 comprise in particular a pair of protrusions 305, the container 300 being configured to receive a pair of supporting elements. In an equivalent alternative embodiment, the coupling means of the container comprise at least one recess configured to allow the insertion of a corresponding protrusion associated to the supporting element.

The side walls of the container 300 have a first supporting flange 302a arranged substantially along a plane which is parallel to the bottom 301 and configured to receive the supporting element. In FIG. 14, showing a sectional view of the supporting element coupled to the container 300 in correspondence with the first supporting flange 302a, a syringe 100 is inserted vertically into one of the through openings 201 and rests on the supporting element at its lobed portions 90.

In order to allow a user to easily remove the supporting element, lifting it from the container 300, the supporting element comprises gripping means such as for example at least one eyelet, at least one cavity, at least one handle, or the like. In the embodiment of FIG. 11 and FIG. 13, the gripping means comprise a pair of cavities arranged at the ends of the central row of the housing cavities for the syringes.

The container 300 comprises a second supporting flange 302b arranged at a height, with respect to the bottom 301, greater than a height of the first flange 302a. Even such second supporting flange 302b is arranged along a plane substantially parallel to the bottom 301 and is configured to be fluid-tightly connected to a sealing element 400. The sealing element 400 can be made of sheet material, for example plastic, apt to define a sealed internal volume of the container 300, in order to avoid any possible contamination of the syringes stored within.

Therefore, if the syringe 100 is of the type described above, the tip cap 20 of the syringe can be arranged in the first stable position (as shown in FIG. 14), given that the maintenance of the sterility of the containment volume 2 is guaranteed by the tightness of the closure of the container 300 by means of the sealing element 400.

The invention claimed is:

1. A device comprising:
a body defining a containment volume for a fluid for medical use, said body comprising a terminal, said terminal defining a conduit configured to put said containment volume into communication with an outside;
a cap support integral with said body and disposed outside said containment volume, said cap support defining an internal volume housing said terminal;
a tip cap associable with said cap support by first constraint means and associable with said terminal by second constraint means, said tip cap being configured to assume at least:
a first stable position in which the tip cap is integral with said cap support, in said first stable position a first portion of the tip cap being housed in the internal volume of said cap support and a second portion of said tip cap emerging from the internal volume of said cap support; and
a second stable position in which the tip cap is integral with said terminal and completely housed in said internal volume of said cap support;
wherein the containment volume is in communication with the outside when said tip cap assumes said first stable position and is sealed when said tip cap assumes said second stable position,
wherein one or more projections emerge from the inner surface of the cap support and are arranged in the internal volume of the cap support,
wherein, when the tip cap is arranged in the second stable position, an end portion of the second portion abuts against a barrier plan defined by the projections, inhibiting or counteracting the transition of the tip cap from the second to the first stable position, and
wherein said projections are configured to:
allow the insertion of the tip cap in the internal volume of the cap support and the transition of the tip cap from the first to the second stable position; and
prohibit or hamper the transition of the tip cap from the second to the first stable position.

2. The device according to claim 1, wherein the first constraint means define a releasable coupling between an inner lateral surface of the cap support and an external lateral surface of the tip cap,
said first constraint means comprising at least one of the following:
at least one undercut defined between the tip cap and the cap support; and
an interference coupling between the tip cap and the cap support.

3. The device according to claim 1, wherein the cap support is integral with the body of the device by means of third constraint means comprising at least one of the following elements:
at least one undercut defined between the cap support and the body;
an interference coupling between the cap support and the body;
one or more seals placed between the cap support and the body, so that the body and the cap support are joined seamlessly;
a coupling by gluing or welding between the cap support and the body of the device;
at least one label made of sheet material;
a sheath placed between the cap support and the body of the device.

4. The device according to claim 3, wherein the third constraint means comprise a weakening portion interposed between the cap support and the body configured for, at least following an external tearing or twisting action exerted on the cap support, being damaged or broken to allow a condition of separation of the cap support from the body and to highlight a tampering with the device, the third constraint means prohibiting a further engagement between the cap support and the body subsequently to the tampering.

5. The device according to claim 3, wherein said label of sheet material or said sheath are placed to connect the cap support with the body.

6. The device according to claim 3, wherein said label of sheet material is glued at the turn of the body and of the cap support or wherein said sheath is shrunk at the turn of the body and of the cap support.

7. The device according to claim 3, wherein said label of sheet material or said sheath have at least one weakening portion or wherein the seals are placed to connect the cap support with the body, defining at least a weakening portion,
wherein the weakening portion are interposed between the cap support and the body and are configured so that, at least after an external tearing or twisting action exerted on the cap support, the label or the seals will result damaged or broken, separating the cap support from the body and highlighting tampering with the device.

8. The device according to claim 1, wherein the tip cap comprises an internal blind cavity configured to receive by insertion, at least when the tip cap is in the second stable position, at least one end portion of the terminal to define a fluid-tight closing between the external environment and the containment volume, said blind cavity being arranged in the first portion of the tip cap and oriented towards the terminal,
  at least one end portion of the first portion of the tip cap being constrained by pressure, at least when the tip cap is in the second stable position, between an external lateral surface of the terminal and the inner surface of the cap support or an inner surface of a collar emerging from the body of the device.

9. The device according to claim 8, wherein the tip cap has:
  a structure made of a first material; and
  a coating made of a second material and arranged:
    on a side surface of the tip cap to engage with the cap support to define the first constraint means; and/or
    at the blind cavity to define the second constraint means;
  the second material having a lower elastic modulus than the elastic modulus of the first material.

10. The device according to claim 8, wherein the cap support comprises a plurality of ridges emerging from an inner side surface of the cap support and arranged in the internal volume of the cap support itself, the ridges joining by interference an external lateral surface of the collar defining at least part of the third constraint means.

11. The device according to claim 8, wherein the collar comprises a threaded coupling portion disposed on an inner lateral surface of the collar itself, said threaded coupling portion being configured to:
  define an axial constraint with the first portion of the tip cap when the latter is placed in the second stable position; and
  define an axial constraint with an auxiliary accessory associable to the terminal by a fluid-tight seal after removing the cap support and the tip cap from the device.

12. The device according to claim 1, wherein the terminal has a conical shape extending between a first end and a second end,
  wherein the first end is constrained to the body of the device and has a first diameter, the second end being free and spaced from the first end and having a second diameter smaller than the first.

13. The device according to claim 12, wherein the terminal is a male Luer-type connector, the connector having a conicity with an angle between 0.5° and 5° with respect to a central axis of the connector.

14. The device according to claim 1, wherein the tip cap has a gripping cavity arranged at least partially at the second portion of the tip cap itself, said gripping cavity defining a concavity of the tip cap delimited by perimetric walls and configured to receive in thrust a coupling member for determining the transition of the tip cap from the first to the second stable position.

15. The device according to claim 14, wherein the perimetric walls of the tip cap cooperate by friction, at least when the tip cap is arranged in the second stable position, with the inner surface of the cap support to inhibit or counteract the transition of the tip cap from the second to the first stable position and
wherein the tip cap and the cap support have a substantially cylindrical shape, the cap support extending in thickness between an outer diameter and an inner diameter, wherein at least the second end portion of the tip cap has a larger diameter than the inner diameter of the cap support, so that the tip cap, when arranged in the second position, is joined by interference fit with the cap support.

16. The device according to claim 15, wherein the tip cap is made of a material whose elastic modulus is lower than the elastic modulus of the material constituting the cap support, in order to facilitate the interference fit of the tip cap in the internal volume of the cap support.

17. The device according to claim 14, wherein the tip cap comprises a centering protrusion emerging from a bottom portion of the gripping cavity and the centering protrusion is entirely arranged in the gripping cavity in correspondence of the axis of symmetry of the tip cap.

18. The device according to claim 17, wherein an annular thrust surface is defined around said centering protrusion.

19. The device according to claim 1, wherein the cap support comprises, in correspondence with an external side wall, a plurality of gripping projections configured to allow or facilitate the grasping of the cap support by a user.

20. The device according to claim 1, wherein the body, the terminal, the cap support and the tip cap have an axisymmetric shape with respect to a same axis.

21. The device according to claim 1, wherein the body has a cylindrical shape extending for a length between 30 mm and 300 mm and a diameter between 5 mm and 40 mm,
  the body being made of a plastic material.

22. A device comprising:
  a body defining a containment volume for a fluid for medical use, said body comprising a terminal, said terminal defining a conduit configured to put said containment volume into communication with an outside;
  a cap support integral with said body and disposed outside said containment volume, said cap support defining an internal volume housing said terminal;
  a tip cap associable with said cap support by first constraint means and associable with said terminal by second constraint means, said tip cap being configured to assume at least:
    a first stable position in which the tip cap is integral with said cap support, in said first stable position a first portion of the tip cap being housed in the internal volume of said cap support and a second portion of said tip cap emerging from the internal volume of said cap support; and
    a second stable position in which the tip cap is integral with said terminal and completely housed in said internal volume of said cap support;
  wherein the containment volume is in communication with the outside when said tip cap assumes said first stable position and is sealed when said tip cap assumes said second stable position,
  wherein one or more projections emerge from the inner surface of the cap support and are arranged in the internal volume of the cap support,
  wherein, when the tip cap is arranged in the second stable position, an end portion of the second portion abuts against a barrier plan defined by the projections, inhibiting or counteracting the transition of the tip cap from the second to the first stable position,
  wherein the tip cap and the cap support have an axisymmetric structure, the first constraint means comprising at least one circumferential groove formed on the outer lateral surface of the tip cap, and one or more reliefs emerging from the inner lateral surface of the cap support towards the internal volume of the cap support, said one or more reliefs being configured to engage said at least one circumferential groove when the tip cap is in the first stable position.

23. The device according to claim 22, wherein at least one of the external lateral surface of the tip cap and the inner lateral surface of the cap support has one or more recesses defining, at least when the tip cap is in the first stable position, one or more gaps between the tip cap and the cap support.

24. The device according to claim 23, wherein said recesses are formed on the inner lateral surface of the cap support and angularly equally spaced apart, developing mainly along substantially parallel directions to an axis of symmetry of the cap support.

25. The device according to claim 23, wherein said projections and said reliefs emerge from the inner lateral surface of the cap support and are interposed between successive recesses according to a repeated angular pattern.

26. The device according to claim 23, wherein the recesses develop along a straight or helical path.

* * * * *